(12) United States Patent
Mickle et al.

(10) Patent No.: US 8,715,699 B2
(45) Date of Patent: *May 6, 2014

(54) AMINO ACID CONJUGATES OF QUETIAPINE, PROCESS FOR MAKING AND USING THE SAME

(75) Inventors: Travis Mickle, Coralville, IA (US); Sven Guenther, Coralville, IA (US); Sanjib Bera, Blacksburg, VA (US)

(73) Assignee: KemPharm, Inc., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/518,981

(22) PCT Filed: Dec. 22, 2010

(86) PCT No.: PCT/US2010/061853
§ 371 (c)(1), (2), (4) Date: Jul. 23, 2012

(87) PCT Pub. No.: WO2011/082076
PCT Pub. Date: Jul. 7, 2011

(65) Prior Publication Data
US 2012/0276168 A1    Nov. 1, 2012

Related U.S. Application Data

(60) Provisional application No. 61/291,576, filed on Dec. 31, 2009.

(51) Int. Cl.
| A61K 31/554 | (2006.01) |
| A61K 9/00 | (2006.01) |
| A61K 33/00 | (2006.01) |
| C07D 417/04 | (2006.01) |
| A61P 25/18 | (2006.01) |
| A61P 25/24 | (2006.01) |
| A61P 25/22 | (2006.01) |

(52) U.S. Cl.
USPC ....... 424/400; 424/722; 514/211.13; 540/551

(58) Field of Classification Search
None
See application file for complete search history.

(56) References Cited

U.S. PATENT DOCUMENTS

| 4,064,138 | A | 12/1977 | Saari et al. |
| 5,527,797 | A | 6/1996 | Eisenberg et al. |
| 5,603,959 | A | 2/1997 | Horrobin et al. |
| 5,955,459 | A | 9/1999 | Bradley et al. |
| 6,022,955 | A | 2/2000 | Sarin et al. |
| 6,197,764 | B1* | 3/2001 | Bradley et al. ............. 514/218 |
| 6,599,897 | B1* | 7/2003 | Brown ..................... 514/211.13 |
| 6,623,752 | B1 | 9/2003 | Fischer et al. |
| 7,060,708 | B2* | 6/2006 | Piccariello et al. ......... 514/282 |
| 2003/0109419 | A1 | 6/2003 | Greengard et al. |
| 2004/0242570 | A1 | 12/2004 | Nudelman et al. |
| 2005/0026899 | A1* | 2/2005 | Goldstein ................ 514/211.13 |
| 2005/0026900 | A1* | 2/2005 | Goldstein ................ 514/211.13 |
| 2005/0171088 | A1 | 8/2005 | Ault et al. |
| 2006/0025567 | A1 | 2/2006 | Collins et al. |
| 2007/0225379 | A1 | 9/2007 | Carrera et al. |
| 2007/0244093 | A1 | 10/2007 | Boehm et al. |
| 2008/0139649 | A1 | 6/2008 | Barrow et al. |
| 2009/0042955 | A1 | 2/2009 | Lynch et al. |
| 2009/0131525 | A1 | 5/2009 | Mickle et al. |
| 2009/0131534 | A1 | 5/2009 | Mickle et al. |
| 2009/0137672 | A1 | 5/2009 | Mickle et al. |
| 2011/0183963 | A1* | 7/2011 | Mickle et al. ............. 514/211.13 |

FOREIGN PATENT DOCUMENTS

| WO | WO 03026563 | 4/2003 |
| WO | WO03026563 | * 4/2003 ............. A61P 25/18 |
| WO | WO 2007004236 | 1/2007 |
| WO | WO 2008050341 | 5/2008 |
| WO | WO 2008079838 | 7/2008 |

OTHER PUBLICATIONS

Partridge, The Bllod-Brain Barrier: Bottleneck in Brain Drug Development, J. Am. Soc. Exper. NeuroTherapeutics, 2005, vol. 2, p. 3-14.*
Cameron et al., Potential Role of a Quetiapine Metabolite in Quetiapine-Induced Neutropenia and Agranuocytosis, Chem. res. Tocicol., 2012, 25, p. 1004-1011 and references cited therein.*
Testa et al. Hydrolysis in Drug and Prodrug Metabolism, Wiley-VCH, 2004, Chapter 4, p. 96-98.*
Matheson et al., Quetiapine, CNS drugs, 2000, vol. 14, pp. 157-172.*
Muller, Prodrug Approaches for Enhancing the bioavailability of Drugs with low solubility, Chem. & Biodiversity, 2009, vol. 6, pp. 2071-2083.*
Gynther et al. and supporting information, Large Amino Acid Transporter Enables Brain Drug Delivery via prodrug, J. Med. Chem., 2008, vol. 51, pp. 932-936, S4, S6.*
International Search Report and Written Opinion for International Patent Application No. PCT/US2010/61853 mailed Feb. 24, 2011.
Cole, P. et al., Quetiapine in Bipolar Disorder: Increasing Evicence of Efficacy and Tolerability, Drugs of Today, vol. 40, No. 10, Oct. 2004, p. 837.
Goodson, in Medical Applications of Controlled Release, supra, vol. 2, pp. 115-138 (1984).
Greene, T.W., "Protective Groups in Organic Synthesis," A Wiley-Interscience Publication, John Wiley & Sons, New York, 1981, pp. 218-287.
Hsien, "Multiple Lamination for Transdermal Patches," Controlled Released Systems Fabrication Technology, v. 1, pp. 167-188 (1988).
Langer, Science, 249:1527-1533 (1990).

(Continued)

*Primary Examiner* — Daniel Sullivan
*Assistant Examiner* — Ping Cao
(74) *Attorney, Agent, or Firm* — McAndrews, Held & Malloy, Ltd.

(57) ABSTRACT

The presently described technology provides a novel class of prodrugs of quetiapine that can be synthesized by chemically conjugating amino acids to quetiapine. The present technology also provides methods of treating patients, pharmaceutical compositions and methods of synthesizing conjugates of the present technology.

13 Claims, 8 Drawing Sheets

(56) References Cited

OTHER PUBLICATIONS

Mahatthanatrakul et al., Int. J. Clin. Pharmacol. Ther., 46(9):489-496 (2008).
Merriam-Webster Dictionary, definition of prodrug, http://www.merriam-webster.com/medical/prodrug, accessed on Nov. 18, 2012.
Pharmacological Basis of Therapeutics, The, 9th Edition, McGraw-Hill (1996) (not submitted—it is an entire reference book that's copyrighted).
Woods, J. Clin. Psychiatry, 64(6):663-667 (2003).
International Search Report and Written Opinion in PCT/US2011/27658, dated Jul. 28, 2011.
Office Action in U.S. Appl. No. 13/043,764, dated Jan. 10, 2012.
Office Action in U.S. Appl. No. 13/043,764, dated Mar. 23, 2012.
IPRP in PCT/US2010/61853 (WO01), dated Jul. 12, 2012.
IPRP in PCT/US2011/27658 (WO02), dated Sep. 20, 2012.
Office Action in U.S. Appl. No. 13/043,764, dated Nov. 26, 2012.
Office Action in U.S. Appl. No. 12/976,546, dated Mar. 28, 2013.
Office Action in U.S. Appl. No. 13/770,462, dated Jul. 11, 2013.
Office Action in U.S. Appl. No. 13/581,496, dated Sep. 6, 2013.

* cited by examiner

Allo-isoleucine tert-Leucine

3-Phenylserine

Isoserine

3-Aminopentanoic acid

2-Amino-octanedioic acid

4-Chloro-β-phenylalanine

β-Homoproline

β-Homoalanine

3-Amino-3-(3-methoxyphenyl)
propionic acid

N-Isobutyryl-cysteine

3-Amino-tyrosine

5-Methyl-tryptophan 2,3-Diaminopropionic Acid

5-Aminovaleric acid 4-(Dimethylamino)cinnamic acid

Phenylalanine-quetiapine (Phe-QTP)

phenylalanine-7-hydroxy-quetiapine (Phe-7-OH-QTP)

phenylalanine-N-desalkyl-quetiapine (Phe-norQTP)

phenylalanine-7-hydroxy-N-desalkyl-quetiapine (Phe-7-OH-norQTP)

_US 8,715,699 B2_

AMINO ACID CONJUGATES OF QUETIAPINE, PROCESS FOR MAKING AND USING THE SAME

RELATED APPLICATIONS

This application claims priority to and benefit from U.S. Provisional Application Ser. No. 61/291,576, filed on Dec. 31, 2009, the content of which is incorporated herein by reference in its entirety.

BACKGROUND OF THE INVENTION

Quetiapine has been used in the treatment of severe mental illness in approximately 70 countries including the US, Canada, most Western European countries, and Japan. Quetiapine is a dibenzothiazepine derivative with a relatively broad receptor binding profile. It has major affinity to cerebral serotonergic ($5\text{-}HT_{2A}$), histaminergic (H1), and dopaminergic $D_1$ and $D_2$ receptors, moderate affinity to $\alpha_1$- and $\alpha_2$-adrenergic receptors, and minor affinity to muscarinergic M1 receptors; it demonstrates a substantial selectivity for the limbic system. This receptor avidity profile with relatively higher affinity for the $5\text{-}HT_{2A}$ receptor compared to the $D_2$ receptor is considered to be, at least in part responsible for the antipsychotic characteristics and low incidence of extrapyramidal side-effects of quetiapine.

The efficacy of quetiapine in reducing positive and negative symptoms of schizophrenia has been proven in several clinical trials with placebo-controlled comparators. Quetiapine has also demonstrated robust efficacy for treatment of cognitive, anxious-depressive, and aggressive symptoms in schizophrenia. Quetiapine has also proven efficacy and tolerability in the treatment of moderate to severe manic episodes, and in the treatment of juveniles with oppositional-defiant or conduct disorders, and in the treatment of the geriatric population with dementia. Data indicate that quetiapine is also effective in the treatment of bipolar depressive symptoms without increasing the risk of triggering manic episodes, and in the treatment of borderline personality disorder. In comparison with other atypical antipsychotics, quetiapine has a favorable side-effect profile.

In clinical trials, only small insignificant prolongations of the QT interval were observed. Weight-gain liabilities and new-onset metabolic side-effects occupy a middle-ground among newer antipsychotics. As a result of its efficacy and tolerability profile, quetiapine has become well established in the treatment of schizophrenia and other psychiatric disorders.

Recently though, in addition to large interindividual variability and weight gain, reports surfaced on treatment emergent diabetes (TED), associated with chronic administration of quetiapine. Additionally, the therapeutical dose of quetiapine is relatively high, forcing the production of pharmaceutical compositions with relatively high concentrations of the active ingredient (up to 60%). Making tablets of such a high concentration of the active pharmaceutical ingredient (API) is difficult, particularly due to the bad tabletting properties of the API.

An advantageous alternative would therefore be to improve the drug's bioavailability, leading to an improved formulation that can lower the total necessary therapeutical dose and/or reduce side-effects such as TED and/or weight gain, and avoid the need for repeated administration. That formulation would help maintain regimen adherence by otherwise reluctant psychiatric patients.

BRIEF SUMMARY OF THE INVENTION

The present technology is directed to a novel class of prodrugs of quetiapine that can be synthesized by chemically conjugating amino acids to quetiapine. The chemical bond between these two moieties is established in one aspect, by reacting a primary hydroxyl functionality of quetiapine or any one of its active metabolites and/or derivatives, with the carboxyl group of the amino acids, thereby creating a carboxylic ester conjugate.

In one embodiment, the invention provides a composition for treating a psychiatric disorder such as schizophrenia, bipolar disorder, obsessive-compulsive disorder, post-traumatic stress disorder, restless legs syndrome, autism, alcoholism, depression, insomnia or Tourette syndrome in a subject, comprising a conjugate of 2-(2-(4-(dibenzo[b,f][1,4]thiazepin-11-yl)piperazin-1-yl)ethoxy)ethanol (quetiapine, QTP) or an active metabolite and/or active derivative thereof; and a standard amino acid such as an aliphatic or aromatic amino acid, non-standard amino acid or synthetic amino acid, a salt thereof, or a combination thereof. In another embodiment, the composition is formulated for oral or rectal administration wherein quetiapine or its active metabolite and/or active derivative thereof such as 7-hydroxy-N-desalkyl-quetiapine (7-OH-norQTP; 4-(7-hydroxydibenzo[b,f][1,4]thiazepin-11-yl)piperazine and a standard amino acid such as an aromatic or aliphatic amino acids, non-standard amino acid or synthetic amino acid, a salt thereof, a derivative thereof or their combination is present in the composition in an amount of about 1-2000 mg/dose based on equimolar weight of unconjugated quetiapine, or unconjugated active metabolite and/or active derivative thereof. Oral administration is carried out in certain embodiments using a tablet, capsule, caplet, pill, troche, lozenge, liquid solution, suspension, elixir, or oral thin film (OTF).

In another embodiment, the invention provides quetiapine or its active metabolite, conjugated to a standard amino acid, i.e., valine as represented by any one of the structures of formulas I-IV:

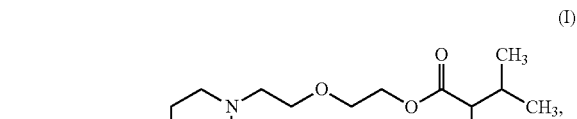

(I)

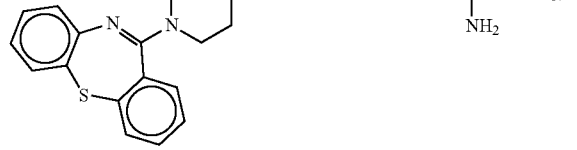

(II)

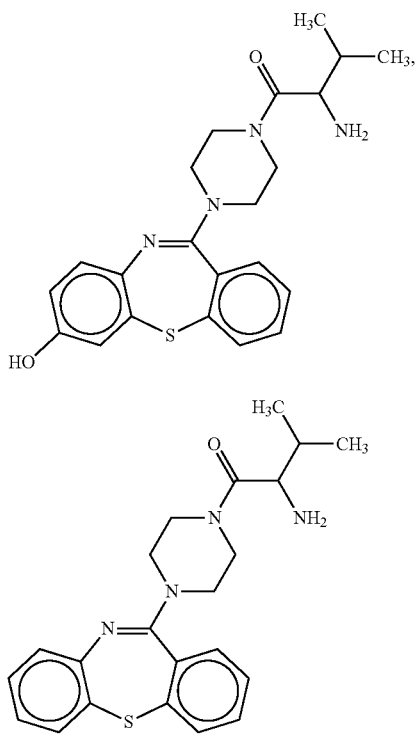

(III)

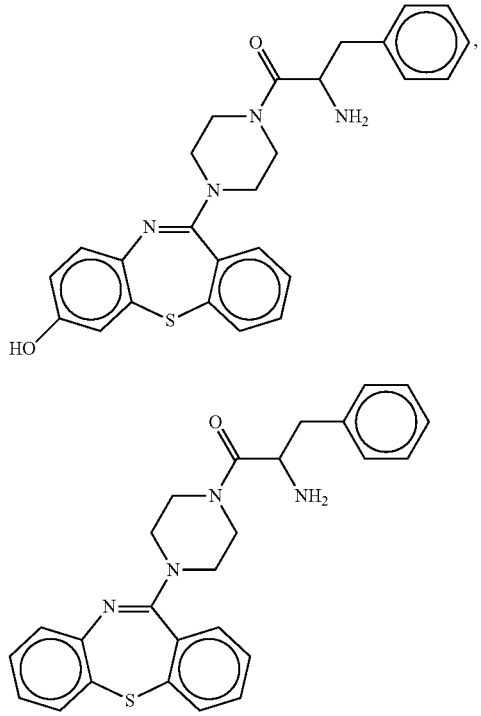

(VII)

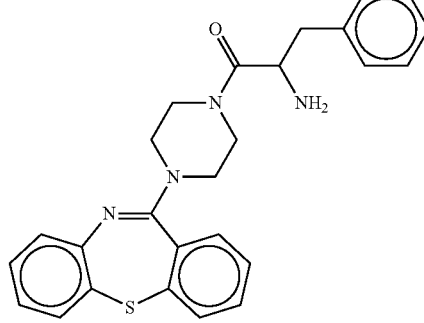

(IV)

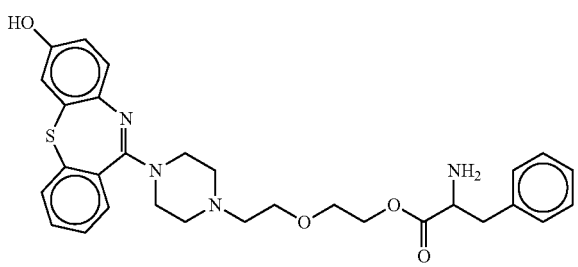

(VIII)

a pharmaceutically acceptable salt thereof such as a phosphate salt, a derivative thereof or their combination.

In one embodiment, the invention provides quetiapine or its active metabolite, conjugated to a standard amino acid i.e., phenylalanine as represented by any one of the structures of formulas V-VIII:

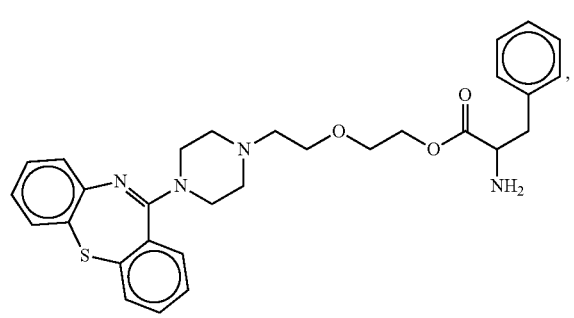

(V)

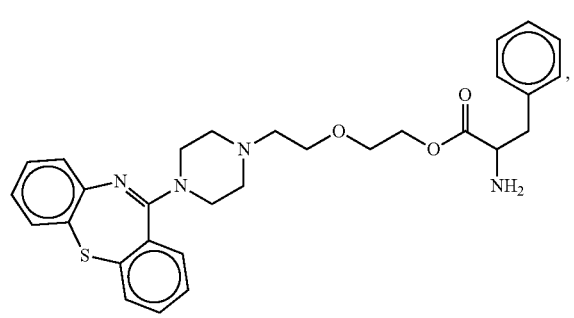

(VI)

a pharmaceutically acceptable salt thereof such as a hydrochloride salt, phosphate salt, mesylate salt or a besylate salt, a derivative thereof or their combination.

In another embodiment, the invention provides a method of conjugating quetiapine or its active metabolite and/or active derivative thereof such as 7-hydroxy-quetiapine (7-OH-QTP) and a standard amino acid such as an aromatic or aliphatic amino acids, non-standard amino acid such as homoarginine or synthetic amino acid, comprising the steps of: in the presence of a base such as 4-methylmorpholine (NMM), 4-(dimethylamino)pyridine (DMAP), attaching an amine-protected amino acid such as an aliphatic or aromatic amino acid to quetiapine or its active metabolite and/or active derivative, whereby the amine moiety is protected with tert-butyloxycarbonyl (Boc) in one embodiment; followed by deprotecting the amine-protected amino acid moiety, alone or either sequentially or simultaneously with deprotecting the amino acid side chain that may be protected as well, thereby conjugating quetiapine or its active metabolite and/or active derivative thereof and an amino acid.

In one embodiment, the invention provides a method of increasing the relative bioavailability of quetiapine or its active metabolite and/or active derivative thereof such as N-desalkyl-quetiapine (norQTP), 7-OH-norQTP or 7-OH-QTP, comprising the step of conjugating the quetiapine or the active metabolite and/or active derivative thereof to a standard amino acid such as an aromatic or aliphatic amino acids, non-standard amino acid such as homoarginine or synthetic amino acid, thereby modulating the hydrophobicity, solubility, improving absorption, altering metabolic pathways or their combination, resulting in certain embodiments, in a higher $C_{max}$ and/or AUC and/or longer or similar $T_{max}$ values produced by unconjugated quetiapine when administered at equimolar doses. Increased bioavailability may also result in: reduced interindividual variability in plasma concentrations; decrease the number and/or amount of active, inactive, toxic or non-toxic metabolites; and increase the number and/or amount of active metabolites produced by unconjugated quetiapine or its active metabolite and/or active derivative thereof.

In another embodiment, the invention provides a method of treating a psychiatric disorder requiring the binding of dopamine receptor(s), serotonin receptor(s), or histamine receptor(s) or a combination thereof in a subject such as human or mammal, comprising the step of orally or rectally administering to the subject a composition comprising a therapeutically effective amount of about 1-2000 mg/dose based on equimolar weight of unconjugated API of quetiapine or its active metabolite and/or active derivative thereof such as N-desalkyl-quetiapine, 7-hydroxy-N-desalkyl-quetiapine, or 7-hydroxy-quetiapine, conjugated to a standard amino acid such as an aromatic or aliphatic amino acids, non-standard amino acid or synthetic amino acid, a pharmaceutically acceptable salt or derivative thereof, thereby binding a dopamine receptor, a serotonin receptor, histamine receptor or any combination permutation thereof. In one embodiment, the invention provides a method of treating schizophrenia or bipolar disorder in a subject in need thereof, comprising the step of administering to the subject a composition comprising a therapeutically effective amount of a quetiapine or its active metabolite and/or active derivative thereof such as N-desalkyl-quetiapine, 7-hydroxy-N-desalkyl-quetiapine, or 7-hydroxy-quetiapine, conjugated to an amino acid, a pharmaceutically acceptable salt such as a phosphate salt, or derivative thereof, thereby binding to a dopamine receptor, a serotonin receptor, or both and treating schizophrenia or bipolar disorder.

In one embodiment, the invention provides a method of reducing weight gain resulting from chronic or acute administration of quetiapine in a subject, comprising the step of orally or rectally administering to the subject a composition comprising therapeutically effective amount of about 1-2000 mg/dose based on equimolar weight of unconjugated API of a quetiapine or its active metabolite and/or active derivative thereof such as N-desalkyl-quetiapine, 7-hydroxy-N-desalkyl-quetiapine, or 7-hydroxy-quetiapine, conjugated to a standard amino acid such as an aromatic or aliphatic amino acids, non-standard amino acid such as homoarginine or synthetic amino acid, a pharmaceutically acceptable salt thereof such as a phosphate salt, or a derivative thereof, thereby modulating leptin and/or gherlin levels in the subject and reducing, decreasing and/or inhibiting weight gain in the subject.

In one embodiment, the invention provides a method of reducing weight gain resulting from chronic or acute administration of quetiapine in a subject, comprising the step of orally or rectally administering to the subject a composition comprising a therapeutically effective amount of about 1-2000 mg/dose based on equimolar weight of unconjugated API of a quetiapine or its active metabolite and/or active derivative thereof such as N-desalkyl-quetiapine, 7-hydroxy-N-desalkyl-quetiapine, or 7-hydroxy-quetiapine, conjugated to a standard amino acid such as an aromatic or aliphatic amino acids, non-standard amino acid such as homoarginine or synthetic amino acid, a pharmaceutically acceptable salt thereof such as a phosphate salt, or a derivative thereof, thereby altering the metabolism of quetiapine, its metabolite(s) and/or derivative(s) resulting in reduced binding to histamine receptors.

In another embodiment, the invention provides for the use of a therapeutically effective amount of a conjugate of quetiapine, its active metabolite and/or active derivative and/or their combination; and a standard, non-standard and/or synthetic amino acid and their combination; in a medicament for the treatment of a disorder associated with serotonin, dopamine or histamine dysfunction in a subject in need thereof.

BRIEF DESCRIPTION OF THE DRAWINGS

The invention will be better understood from a reading of the following detailed description taken together with the figures and examples provided herein wherein like reference designators are used to designate like elements or findings, and in which.

DETAILED DESCRIPTION OF THE INVENTION

Figure 1:
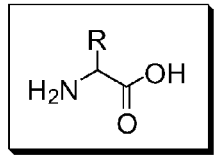
FIG. 1 shows general structure of standard amino acids.

In one embodiment, the invention is directed to quetiapine conjugate compositions, their synthesis and use. In another embodiment, the invention is directed to quetiapine conjugates with standard, non-standard or synthetic amino acids, their syntheses and use in therapeutic compositions for the treatment of psychiatric disorders.

Quetiapine:

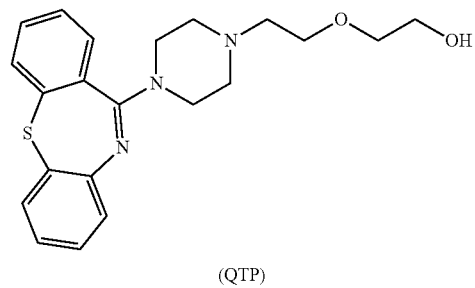 [SMILES: OCCOCCN1CCN(C2=Nc3ccccc3Sc3ccccc32)CC1]

(QTP)

is an atypical antipsychotic in the sub-class of multi-acting receptor-targeted antipsychotics (MARTA). Quetiapine exhibits antagonist activity at the dopamine $D_2$ and $D_1$ receptors, the serotonin 5-$HT_2$ receptor, the adrenergic $a_1$ and $a_2$ receptors and the histamine $H_1$ receptor. While the modulation of the dopamine and serotonin receptors are thought to be responsible for the therapeutic activity of quetiapine, its affinity to the histamine and adrenergic receptors may be the cause of some of its side-effects, particularly its somnolent and hypotensive effects.

Quetiapine is currently approved for the following indications:

Acute and chronic treatment of schizophrenia.

Acute depressive episodes associated with bipolar disorder.

Acute manic or mixed episodes associated with bipolar I disorder as monotherapy and as an adjunct to lithium or divalproex therapy.

Chronic treatment of bipolar I disorder as adjunct therapy to lithium or divalproex.

Quetiapine has also shown acceptable efficacy in some off-label indications that include obsessive-compulsive disorder, post-traumatic stress disorder, restless legs syndrome, autism, alcoholism, depression and Tourette syndrome. It has been used as sedative for patients with sleep or anxiety disorders.

In one embodiment, the compositions comprising the prodrugs provided herein may be administered for the treatment of schizophrenia or bipolar disorder or for any condition that may require the blocking of dopamine or serotonin receptors.

The term "prodrug", as used herein, refers in one embodiment to a metabolic precursor of a compound of the conjugated quetiapine provided herein, which is pharmaceutically acceptable. A prodrug may be inactive when administered to a subject but is converted in vivo to an active compound. In one embodiment, the term "active metabolite", refers to a metabolic product of quetiapine that is pharmaceutically and/or pharmacologically beneficial and/or effective. Prodrugs and active metabolites may be determined using techniques known in the art. Prodrugs and active metabolites of a compound may be identified using routine techniques known in the art. In another embodiment, the term "active metabolite" refers to a metabolic product of quetiapine that is effective for ameliorating, treating or preventing schizophrenia, bipolar disorder, obsessive-compulsive disorder, post-traumatic stress disorder, restless legs syndrome, autism, alcoholism, depression, insomnia or Tourette syndrome.

Prodrugs are often useful because, in some embodiments, they may be easier to administer or process than the parent drug. They may, for instance, be bioavailable by oral administration whereas the parent is not. The prodrug may also have improved solubility in pharmaceutical compositions over the parent drug. An embodiment of a prodrug would be an amino acid bonded to a primary hydroxyl group where the amino acid is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism or the transport characteristics of a drug in certain embodiments, to mask side-effects or toxicity, to improve the flavor of a drug or to alter other characteristics or properties of a drug in other discrete embodiments. By virtue of knowledge of pharmacodynamic processes and drug metabolism in vivo, those of skill in this art, once a pharmaceutically active compound is known, can design prodrugs of the compound.

In another embodiment, the term "active metabolite" refers to a biologically active derivative of a compound that is formed when the compound is metabolized. The term "metabolized," refers in one embodiment to the sum of the processes (including, but not limited to, hydrolytic reactions and reactions catalyzed by enzymes, such as, oxidation reactions, de-esterification reactions and/or proteolytic reactions) by which a particular substance is changed by an organism. Thus, enzymes may produce specific structural alterations to a compound. In one embodiment, cytochrome P450 catalyzes a variety of oxidative and reductive reactions while some isoforms, such as CYP3A4 are involved in de-esterification. Further information on metabolism may be obtained from The Pharmacological Basis of Therapeutics, 9th Edition, McGraw-Hill (1996). Metabolites of the compounds disclosed herein can be identified either by administration of compounds to a host under conditions allowing for the determination of activity by the metabolite and analysis of tissue samples from the host, or by incubation of compounds with hepatic cells in vitro and analysis of the resulting compounds. Both methods are well known in the art. In some embodiments, a compound is metabolized to pharmacologically active metabolites.

In another embodiment, amino acids conjugated to quetiapine or its active metabolite and/or derivative create ester prodrugs that can release the active antipsychotic. The prodrugs provided herein alter the pharmacology and/or metabolism of quetiapine its active metabolite and/or derivative. As a result; by choosing suitable amino acids, the bioavailability of quetiapine is increased. In one embodiment, the side-effect profile and interindividual variability in plasma concentrations of the active are improved.

In one embodiment, provided herein is a novel class of prodrugs of quetiapine its active metabolite and/or derivative, which is synthesized by chemically conjugating amino acids to quetiapine its active metabolite and/or derivative. The chemical bond between these two moieties is established by reacting the primary hydroxyl functionality of quetiapine, its active metabolite and/or derivative or non-binding electrons with the carboxyl group of the amino acids, thereby creating an ester conjugate.

Accordingly and in another embodiment, provided herein is a composition for treating a psychiatric disorder in a subject, comprising a conjugate of 2-(2-(4-(dibenzo[b,f][1,4]thiazepin-11-yl)piperazin-1-yl)ethoxy)ethanol (quetiapine) its active metabolite and/or derivative and an amino acid, a salt thereof, a derivative thereof or their combination.

All amino acids have a core structure containing an amino group, a carboxyl group and a distinctive side chain. The carbon atom attached to the carboxyl group is called the α-carbon. In α-amino acids both the amino and carboxyl group are attached to the α-carbon. In amino acids with a carbon side chain attached to the α-carbon, the carbons are labeled in the order of α, β, γ, δ, ε, etc. Amino acids with the amino group attached to a carbon other than the α-carbon are respectively called β-amino acids, γ-amino acids, δ-amino acids and so forth. Amino acids can be either D or L isomers. This invention includes compounds obtained by conjugation of quetiapine to L and/or D isomers of amino acids including but not limited to α-, β-, γ-, δ, ε-amino acids, standard amino acids, non-standard amino acids, natural amino acids and synthetic (unnatural/non-natural) amino acids.

Depending on the side chain of the amino acids conjugated to quetiapine or its active metabolite, the prodrug formed can be either neutral in one aspect of the invention, or free acid, free base or pharmaceutically acceptable anionic or cationic salt forms or salt mixtures with any ratio between positive and negative components in other discrete aspects. These salt forms include, but are not limited to: acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate. In one embodiment, composition for treating a psychiatric disorder in a subject, comprising a conjugate of 2-(2-(4-(dibenzo[b,f][1,4]thiazepin-11-yl)piperazin-1-yl) ethoxy)ethanol (quetiapine) its active metabolite and/or derivative; and an amino acid are in the form of a phosphate salt.

In the compositions and methods described herein, the synthesized prodrugs are designed to breakdown enzymatically or otherwise in vivo to quetiapine, its active metabolites and/or derivatives and the respective amino acids or their metabolites. Preferably, the amino acids of the present technology are Generally Regarded As Safe (GRAS) or non-toxic at the concentrations released into the systemic circulation.

The amino acids used in the compositions and methods described herein, can be broadly classified in one of the following categories: standard (proteinogenic) amino acids; non-standard amino acids; and synthetic (unnatural/non-natural) amino acids.

Standard Amino Acids

Standard amino acids or proteinogenic amino acids include but are not limited to the currently known 22 amino acids that make up the monomeric units of proteins and are encoded in the standard genetic code. Standard amino acids include alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine. These amino acids have the general structure shown in FIG. 1, where R represents the side chain on the $\alpha$-carbon. In one embodiment, the compositions provided herein, which are used in the methods provided, comprise quetiapine or its antipsychotic-active metabolites, conjugated to a standard amino acid, wherein the standard amino acid is alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine or valine, their derivatives and pharmaceutically acceptable salts. Accordingly and in one embodiment, the amino acid conjugated to quetiapine or its active metabolite, used in the compositions and methods described herein, is an aliphatic or aromatic amino acid wherein the aliphatic amino acid is glycine, leucine, isoleucine, proline, valine, methionine or alanine and/ or, in another embodiment the aromatic amino acid is histidine, phenylalanine, tryptophan or tyrosine.

Non-Standard Amino Acids

Figure 2:
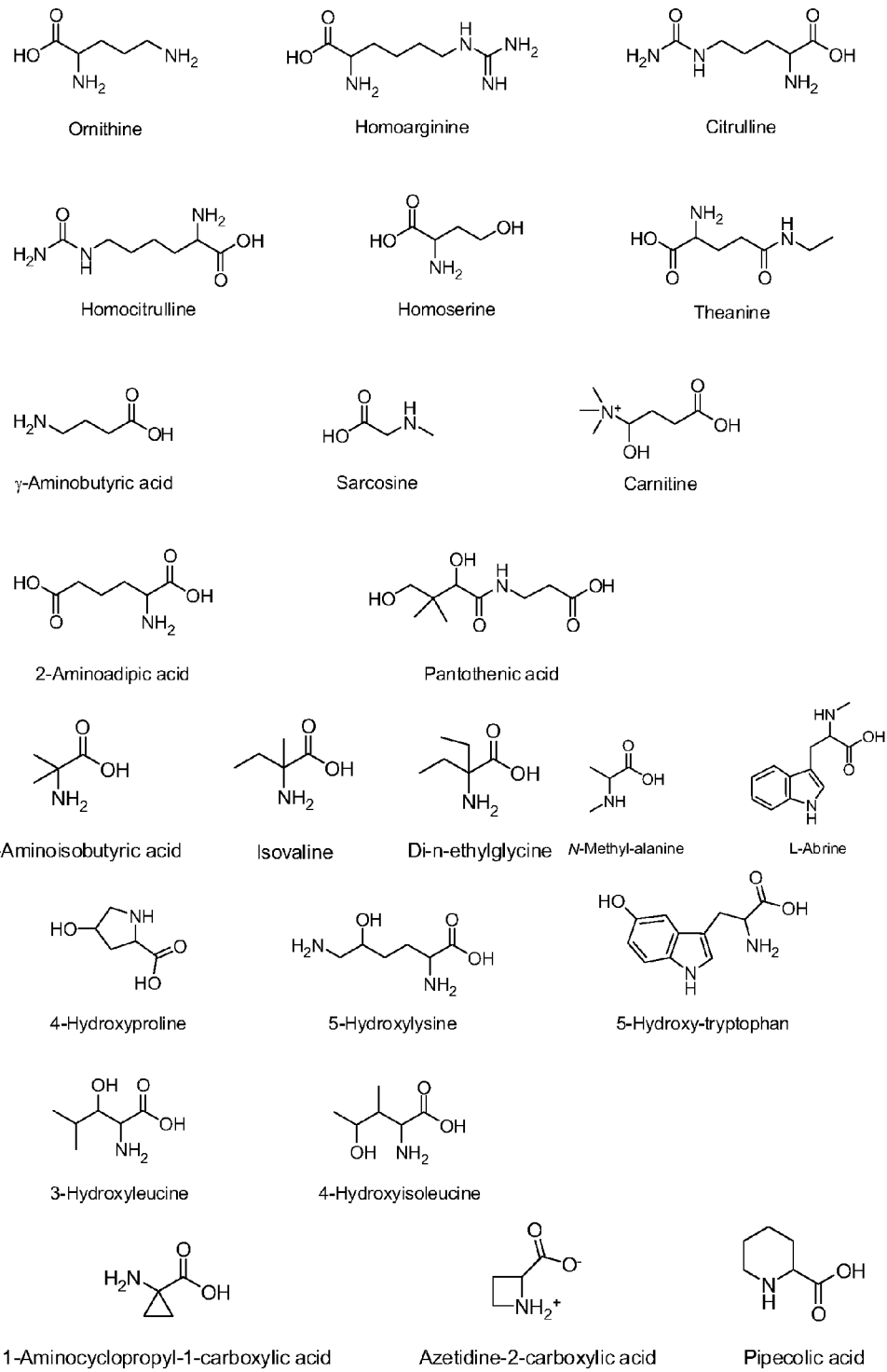
FIG. 2 shows general structure of non-standard amino acids.
Figure 3A:
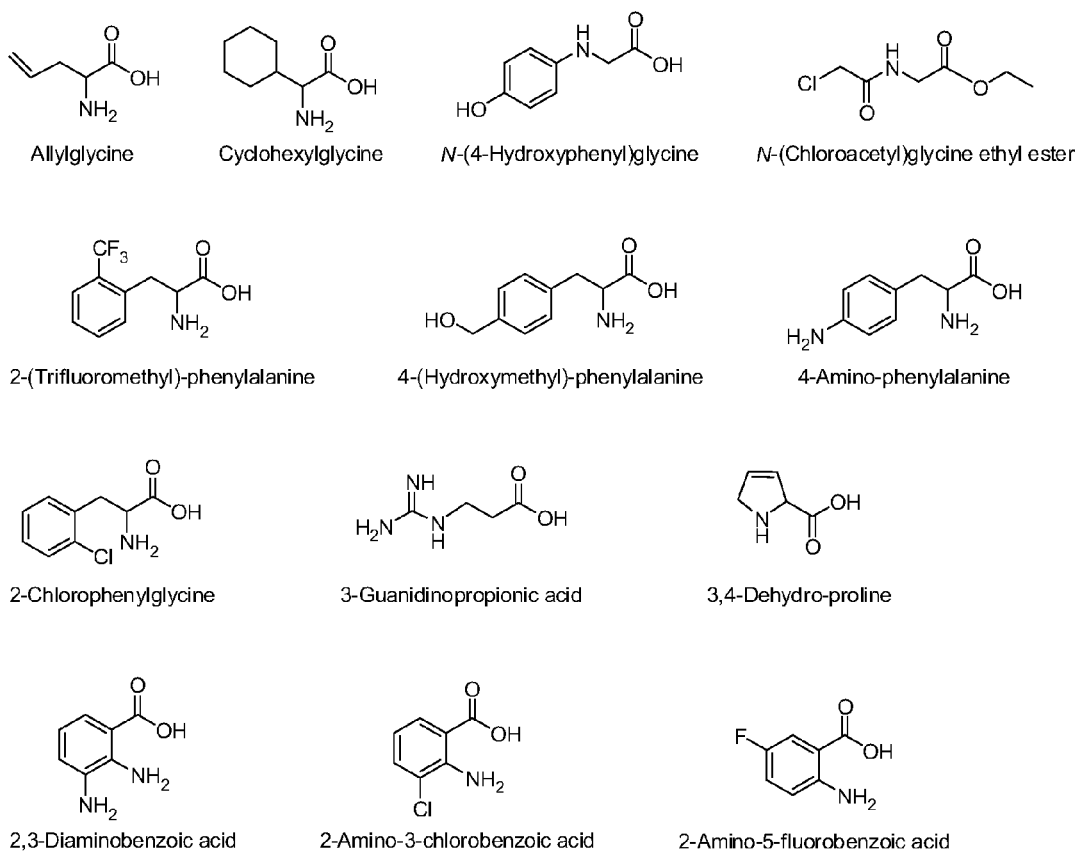
FIG. 3 shows synthetic amino acids.
Figure 3B:
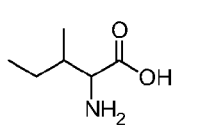
Figure 3B:
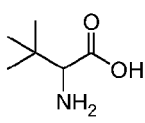
Figure 3B:
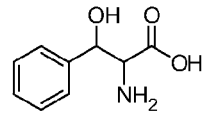
Figure 3B:
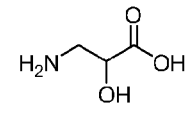
Figure 3B:
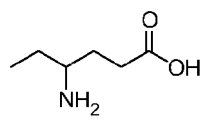
Figure 3B:
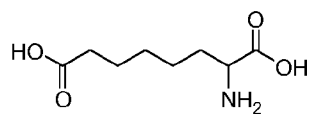
Figure 3B:
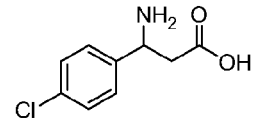
Figure 3B:
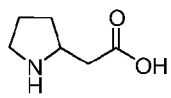
Figure 3B:
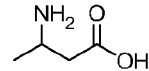
Figure 3B:
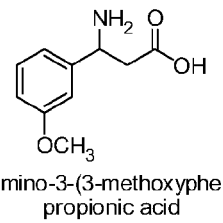
Figure 3B:
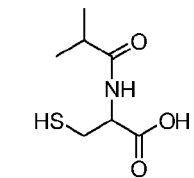
Figure 3B:
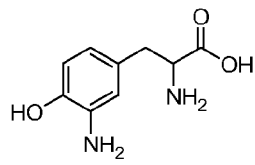
Figure 3B:
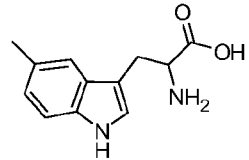
Figure 3B:
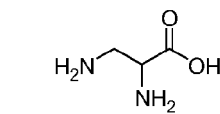
Figure 3B:
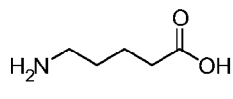
Figure 3B:
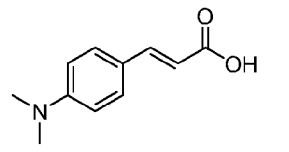

Non-standard amino acids can be found in proteins created by chemical modifications of standard amino acids already incorporated in the proteins. This group also includes amino acids that are not found in proteins but are still present in living organisms. Non-standard amino acids occur mostly as intermediates in metabolic pathways of standard amino acids and are not encoded by the standard genetic code. Examples of non-standard amino acids include but are not limited to ornithine, homoarginine, citrulline, homocitrulline, homoserine, theanine, γ-aminobutyric acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid (FIG. 2).

In one embodiment, the compositions provided herein, which are used in the methods provided, comprise quetiapine or its antipsychotic-active metabolites, conjugated to a non-standard amino acid, wherein the non-standard amino acid is ornithine, homoarginine, citrulline, homocitrulline, homoserine, theanine, γ-aminobutyric acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid or pipecolic acid, their derivatives and pharmaceutically acceptable salts.

Synthetic Amino Acids

Synthetic amino acids do not occur in nature and are prepared synthetically. In another embodiment, the compositions provided herein, which are used in the methods provided, comprise quetiapine or its antipsychotic-active metabolites, conjugated to a non-standard amino acid that includes but is not limited to allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-aminooctanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, and 4-(dimethylamino)cinnamic acid (FIG. 3).

In one embodiment, the compositions provided herein, which are used in the methods provided, comprise quetiapine or its antipsychotic-active metabolites, conjugated to a synthetic amino acid, wherein the synthetic amino acid is allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, or 4-(dimethylamino)cinnamic acid, their derivative or pharmaceutically acceptable salt and their combination.

In one aspect of the invention any of the abovementioned amino acids; standard (proteinogenic) amino acids; non-standard amino acids; and synthetic (unnatural/non-natural) amino acids are used either alone or in combination in the compositions and methods described herein. Accordingly and in one embodiment, provided herein is a composition for treating a psychiatric disorder in a subject, comprising a conjugate of 2-(2-(4-(dibenzo[b,f][1,4]thiazepin-11-yl)piperazin-1-yl)ethoxy)ethanol (quetiapine), its active metabolite and/or derivative and their combination; and a standard amino acid, a non-standard amino acid, or a synthetic amino acid; a salt thereof, a derivative thereof or their combination.

In another embodiment, the amino acid conjugated to quetiapine, its active metabolite and/or derivative and their combination, used in the compositions and methods described herein, is an aliphatic amino acid, such as glycine in one embodiment. In other embodiments the aliphatic amino acids used in the compositions and methods described herein are leucine, isoleucine, valine, proline, methionine or alanine each a discrete embodiment of the aliphatic amino acids used in the conjugates of quetiapine, its active metabolite and/or derivative and their combination provided herein.

In one embodiment, the active metabolite of quetiapine is N-desalkyl-quetiapine (norQTP, 4-(dibenzo[b,f][1,4]thiazepin-11-yl)piperazine):

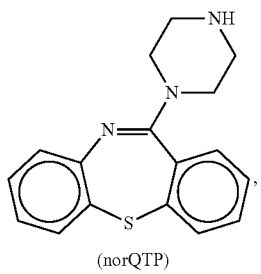

(norQTP)

a major active human plasma metabolite of quetiapine, which has shown in-vitro antagonistic activity on multiple brain neurotransmitter receptors and in particular on serotonergic (5-HT$_{2A}$), noradrenergic ($\alpha_1$-adrenoreceptor) and the noradrenergic transporter, thus having in another embodiment, a positive influence on mood. Likewise, N-desalkyl-quetiapine has a high affinity for the histamine H$_1$ receptor and moderate affinities for the norepinephrine reuptake transporter (NET), the serotonin 5-HT$_{1A}$, 5-HT$_{1E}$, 5-HT$_{2A}$, 5-HT$_{2B}$, 5-HT$_7$ receptors, the $\alpha_{1B}$-adrenergic receptor, and the M$_1$, M$_3$, and M$_5$ muscarinic receptors. In one embodiment, N-desalkyl-quetiapine has about 100-fold higher avidity for inhibiting human NET than quetiapine itself. Additionally, N-desalkyl-quetiapine is 10-fold more potent and more efficacious than quetiapine at the 5-HT$_{1A}$ receptor. N-desalkyl-quetiapine is an antagonist at 5-HT$_{2A}$, 5-HT$_{2B}$, 5-HT$_{2C}$, $\alpha_{1A}$, $\alpha_{1D}$, $\alpha_{2A}$, $\alpha_{2C}$, H$_1$, M$_1$, M$_3$, and M$_5$ receptors, with a moderate affinity for the norepinephrine reuptake inhibitor transporter (NET) and partial 5-HT1$_A$ agonism, indicating a significant antidepressant effects. In one embodiment, the compositions provided herein, which in another embodiment are used in the methods provided herein comprise the N-desalkyl-quetiapine, conjugated to a standard, non-standard or synthetic amino acid, without the presence of quetiapine.

In one embodiment, the active metabolite of quetiapine is 7-hydroxy-quetiapine (2-(2-(4-(7-hydroxydibenzo[b,f][1,4]thiazepin-11-yl)piperazin-1-yl)ethoxy)ethanol):

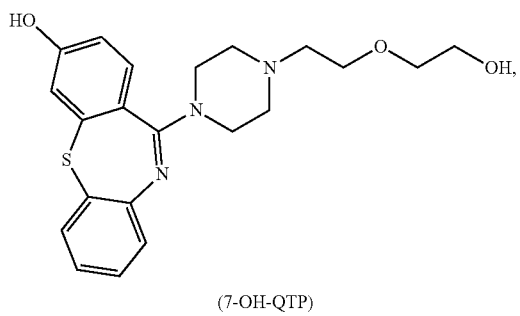 [SMILES: OCCOCCN1CCN(C2=Nc3ccccc3Sc3cc(O)ccc32)CC1]

(7-OH-QTP)

another active human plasma metabolite of quetiapine having intrinsic receptor activity. 7-hydroxy-quetiapine has been shown to occupy dopamine D$_2$ and serotonin 5-HT$_2$ receptors. In one embodiment, the compositions provided herein, which in another embodiment are used in the methods provided herein comprise 7-hydroxy-quetiapine, conjugated to a standard, non-standard or synthetic amino acid, without the presence of quetiapine.

In another embodiment, the term "derivative" refers to having a substituent bonded to the quetiapine or its active metabolite such as halogenated derivatives ether derivatives, acid derivatives, amide derivatives, ester derivatives and the like. Methods of preparing derivatives such as ether derivatives in one embodiment, comprise coupling of the corresponding alcohols. In another embodiment, the term "derivative" refers to a chemical compound related structurally to quetiapine or its active metabolites and is therapeutically derivable from it. In one embodiment, the term "active derivative" refers to a derivative as defined herein, which is accountable for a desired biological effect. Accordingly, an active derivative of quetiapine will have in one embodiment an antipsychotic activity, or an antidepressant activity and the like in other embodiments of desired biological effect.

In one embodiment, the active derivative of quetiapine is 2-chloro-N-desalkyl-quetiapine (2-chloro-11-(piperazin-1-yl)dibenzo[b,f][1,4]thiazepine);

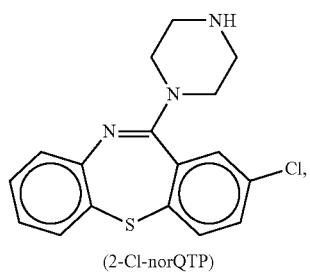

(2-Cl-norQTP)

a derivative of norQTP, which, due to its similar structure to the known antidepressant Amoxapine (sold as ASENDIN, ASENDIS, DEFANYL, DEMOLOX, MOXADIL), is thought to possess similar activity as a norepinephrin reuptake inhibitorand and/or as a partial 5-HT agonist. In one embodiment, the compositions provided herein, which in another embodiment is used in the methods provided herein comprise 2-chloro-N-desalkyl-quetiapine, conjugated to a standard, non-standard or synthetic amino acid and/or its pharmaceutically acceptable salt, without the presence of quetiapine.

In one embodiment, the active derivative of quetiapine is 4-(7-hydroxydibenzo[b,f][1,4]thiazepin-11-yl)piperazine, 7-hydroxy-N-desalkyl-quetiapine (7-OH-norQTP);

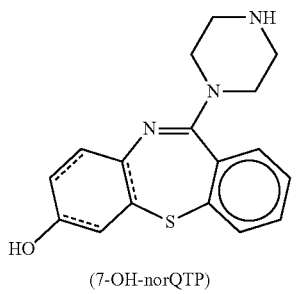

(7-OH-norQTP)

a derivative of norQTP, which, due to its similar structure to the known active quetiapine metabolite 7-hydroxy-quetiapine, is thought to possess similar activity. In one embodiment, the compositions provided herein, which in another embodiment is used in the methods provided herein comprise 7-hydroxy-N-desalkyl-quetiapine, conjugated to a standard, non-standard or synthetic amino acid and/or its pharmaceutically acceptable salt, without the presence of quetiapine.

In one embodiment, the amino acid is valine and the conjugate is 2-(2-(4-(dibenzo[b,f][1,4]thiazepin-11-yl)piperazin-1-yl)ethoxy)ethyl L-valine, 2-(2-(4-(dibenzo[b,f][1,4]thiazepin-11-yl)piperazin-1-yl)ethoxy)ethyl D-valine, 2-(2-(4-hydroxydibenzo[b,f][1,4]thiazepin-11-yl)piperazin-1-yl)ethoxy)ethyl L-valine, 2-(2-(4-(7-hydroxydibenzo[b,f][1,4]thiazepin-11-yl)piperazin-1-yl)ethoxy)ethyl D-valine, (R)-2-amino-1-(4-(dibenzo[b,f][1,4]thiazepin-11-yl)piperazin-1-yl)-3-methylbutan-1-one, (S)-2-amino-1-(4-(dibenzo[b,f][1,4]thiazepin-11-yl)piperazin-1-yl)-3-methylbutan-1-one, (R)-2-amino-1-(4-(7-hydroxydibenzo[b,f][1,4]thiazepin-11-yl)piperazin-1-yl)-3-methylbutan-1-one, (S)-2-amino-1-(4-(7-hydroxydibenzo[b,f][1,4]thiazepin-11-yl)piperazin-1-yl)-3-methylbutan-1-one; their derivative, pharmaceutically acceptable salt or their combination.

In one embodiment, the amino acid is phenylalanine and the conjugate is 2-(2-(4-(dibenzo[b,f][1,4]thiazepin-11-yl)piperazin-1-yl)ethoxy)ethyl L-phenylalanine, 2-(2-(4-(dibenzo[b,f][1,4]thiazepin-11-yl)piperazin-1-yl)ethoxy)ethyl D-phenylalanine,2-(2-(4-(7-hydroxydibenzo[b,f][1,4]thiazepin-11-yl)piperazin-1-yl)ethoxy)ethyl L-phenylalanine, 2-(2-(4-(7-hydroxydibenzo[b,f][1,4]thiazepin-11-yl)piperazin-1-yl)ethoxy)ethyl D-phenylalanine, (R)-2-amino-1-(4-(dibenzo[b,f][1,4]thiazepin-11-yl)piperazin-1-yl)-3-phenylpropan-1-one, (S)-2-amino-1-(4-(dibenzo[b,f][1,4]thiazepin-11-yl)piperazin-1-yl)-3-phenylpropan-1-one, (R)-2-amino-1-(4-(7-hydroxydibenzo[b,f][1,4]thiazepin-11-yl)piperazin-1-yl)-3-phenylpropan-1-one, (S)-2-amino-1-(4-(7-hydroxydibenzo[b,f][1,4]thiazepin-11-yl)piperazin-1-yl)-3-phenylpropan-1-one; their derivative, pharmaceutically acceptable salt or their combination.

Amino acid ester prodrugs of quetiapine, its active metabolite and/or derivative and their combination as described above can be administered orally and the parent drug is released after hydrolysis in the body. Typically these prodrugs are easily recognized by physiological systems because the attached amino acid moieties are either naturally occurring or mimic naturally occurring compounds. As a result, the prodrugs provided herein are hydrolyzed chemically, enzymatically or by a combination of chemical and enzymatic processes; and release quetiapine. In another embodiment the compositions comprising the prodrug described herein, are either pharmacologically inactive, have pharmacological activity that is limited or different from the parent drug, and consequently, in certain embodiments, may follow a metabolic pathway that differs from quetiapine.

In another embodiment, the term "prodrug" refers to a precursor or derivative form of a pharmaceutically active substance that imparts higher bioavailability to quetiapine compared to the parent drug and is capable of being enzymatically or hydrolytically activated or converted into the more active parent form. In one embodiment, the compositions comprising the prodrug described herein would release quetiapine, its active metabolite and/or derivative and their combination—in a similar fashion, to free or unconjugated API. In another embodiment, the compositions comprising the prodrug described herein would release quetiapine, its active metabolite and/or derivative or their combination—in a controlled or sustained manner without the need of an extended release formulation.

In a further embodiment, the compositions comprising the prodrug described herein would have increased absorption over unmodified quetiapine. In another embodiment, the compositions comprising the prodrug described herein would have improved water solubility over free quetiapine. In another embodiment, the increased absorption over unmodified quetiapine, or improved water solubility over free quetiapine, provide for a better bioavailability of quetiapine referring to a higher area under the curve (AUC) or having higher circulating plasma concentrations.

In another embodiment, conjugating quetiapine, its therapeutically active metabolite(s) and/or derivative(s) to a standard, non standard or synthetic amino acid as well as their pharmaceutically accepted salts, alter the API metabolism, thereby resulting in a maximum plasma concentration ($C_{max}$) value of released quetiapine that is higher than the $C_{max}$ value produced by unconjugated quetiapine when administered at equimolar doses, or in generating an AUC value of released quetiapine that is higher than the AUC value produced by unconjugated quetiapine in another embodiment, or in generating both a $C_{max}$ and an AUC value of released quetiapine that is higher than the $C_{max}$ and AUC values produced by unconjugated quetiapine, or in generating a time after administration at which $C_{max}$ occurs ($T_{max}$) value of released quetiapine its active metabolite and/or derivative and their combination that is longer than the $T_{max}$ value produced by unconjugated quetiapine, or in generating a $T_{max}$ value of released quetiapine that is similar to the $T_{max}$ value produced by unconjugated quetiapine, when administered at equimolar or therapeutically equivalent doses.

In one embodiment, the term "therapeutically equivalent" refers to a preparation where its therapeutic effect is equivalent. In another embodiment, the term "therapeutically equivalent" refers to circumstances where conjugated quetiapine, its therapeutically active metabolite(s) and/or derivative(s) and their pharmaceutically acceptable salts as described herein, are administered in amounts which give rise to the same therapeutic effect as does the specified amount of unconjugated quetiapine, its therapeutically active metabolite(s) and/or derivative(s) and their pharmaceutically acceptable salts. It is routine for those skilled in the art to determine therapeutically equivalent amounts or dosages (see e.g. Mahatthanatrakul et al., Int J Clin Pharmacol Ther. 2008 September; 46(9):489-96. and/or Woods, S. W. J Clin Psychiatry. 2003 June; 64(6):663-7)

In another embodiment, the terms "therapeutically effective", or "therapeutic effect", refers to that amount of the conjugated or unconjugated API being administered, which will relieve to some extent one or more of the symptoms of the disorder or disease being treated. In another embodiment, the term "therapeutically effective dose" refers to the amount of a compound of the compositions described herein that, when administered to an individual is effective to at least partially treat a disorder, disease or condition from which the individual is suffering, or to at least partially ameliorate a symptom of such disorder, disease or condition. As is understood in the art, the therapeutically effective amount of a given compound will depend at least in part upon, the mode of administration, any carrier or vehicle (e.g., solution, emulsion, etc.) employed, the specific disorder or condition, other medications taken by the individual and the specific characteristics of the individual to whom the compound is to be administered (age, weight, condition, sex, etc.).

In yet another embodiment, the compositions comprising the prodrug described herein would have increased bioavailability over unconjugated quetiapine. This may allow for administration of a lower dose with equal or improved therapeutic effect, but with fewer and/or less severe side-effects when compared to unmodified quetiapine, thereby improving the safety and/or tolerability profile of the drug. Common side-effects associated with quetiapine include sedation, numbing, constipation, dizziness, dry mouth, lightheadedness, nasal congestion, sore throat, stomach pain or upset, tiredness, vomiting, weakness, weight gain, hyperlipidemia, hypotension, hyperglycemia and more. In one embodiment, the use of the compositions described herein results in elimination, amelioration, reduction, delay of onset or improvement in common side-effects associated with chronic or acute administration of quetiapine, wherein the common side-effects include but are not limited to sedation, constipation, dizziness, dry mouth, lightheadedness, nasal congestion, sore throat, stomach pain or upset, tiredness, vomiting, weakness, weight gain, hyperlipidemia, hypotension, hyperglycemia or their combination.

In another embodiment, the compositions comprising the prodrug described herein would reduce weight gain when compared to unconjugated quetiapine. Accordingly and in one embodiment, the invention provides a method of reducing weight gain resulting from chronic or acute administration of quetiapine in a subject, comprising the step of orally or rectally administering to the subject a composition comprising a therapeutically effective amount of about 1-2000 mg/dose based on equimolar weight of unconjugated quetiapine; of quetiapine or its active metabolite and/or active derivative thereof such as 7-hydroxy-N-desalkyl-quetiapine, or 7-hydroxy-quetiapine, conjugated to a standard amino acid such as an aromatic or aliphatic amino acids, non-standard amino acid such as homoarginine or synthetic amino acid, a pharmaceutically acceptable salt such as a phosphate salt or derivative thereof, thereby modulating leptin and/or gherlin levels, or in another embodiment, altering the metabolism of quetiapine, its metabolite(s) and/or derivative(s), resulting in reduced binding to histamine receptor(s) in the subject and thereby eliminating, reducing, delaying, decreasing and/or inhibiting weight gain in the subject.

In one embodiment, chronic oral administration of quetiapine, a known orexigenic, for a period of 6 weeks causes about 37% increase in leptin release. In another embodiment, conjugating an active metabolite and/or derivative of quetiapine to a standard, non-standard or synthetic amino acid will decrease the release of leptin and/or gherlin, resulting in certain embodiments in lower weight gain or lower increase in body-mass index (BMI). Since gherlin regulates the release of leptin in certain embodiment, and is released in response to fasting and cachexia, ingestion of aliphatic and aromatic amino acid conjugates of quetiapine will decrease its release, resulting in lower weight gain.

In one embodiment, provided herein is a method of reducing weight gain resulting from chronic or acute administration of quetiapine in a subject, comprising the step of orally or rectally administering to the subject a composition comprising a therapeutically effective amount of about 1-2000 mg/dose based on equimolar weight of unconjugated API of a quetiapine or its active metabolite and/or active derivative thereof such as N-desalkyl-quetiapine, 7-hydroxy-N-desalkyl-quetiapine, or 7-hydroxy-quetiapine, conjugated to a standard amino acid such as an aromatic or aliphatic amino acids, non-standard amino acid such as homoarginine or synthetic amino acid, a pharmaceutically acceptable salt thereof such as a phosphate salt, or a derivative thereof, thereby altering the metabolism of quetiapine, its metabolite(s) and/or derivative(s) resulting in reduced binding to histamine receptors.

In one embodiment $H_1$-histamine receptor antagonism increases feeding in rodents. Additionally, in another embodiment, depletion of neuronal histamine increases feeding. Likewise $H_1$-knockout mice are relatively resistant to the anorectic actions of leptin, and are prone to obesity when placed on high-fat diets. These results indicate that in one embodiment, $H_1$-histamine receptors modulate feeding behavior via a leptin-dependent mechanism. In another embodiment, $H_1$ affinity is a predictor of weight gain in chronic administration of antipsychotic. In one embodiment, the conjugated quetiapine, its therapeutically effective metabolite(s) and/or derivative(s) reduces the affinity of quetiapine to $H_1$ receptor, raising the $K_m$ in one embodiment above 11 nM.

In another embodiment, the compositions comprising the prodrug described herein would generate a $C_{max}$ value of released quetiapine that is higher than the $C_{max}$ value produced by unconjugated quetiapine when administered at equimolar doses. In a further embodiment, the compositions comprising the prodrug described herein would generate an AUC value of released quetiapine that is higher than the AUC value produced by unconjugated quetiapine when administered at equimolar doses. In yet another embodiment, the compositions comprising the prodrug described herein would generate both a $C_{max}$ and an AUC value of released quetiapine that is higher than the $C_{max}$ and AUC values produced by unconjugated quetiapine when administered at equimolar doses.

In another embodiment the compositions comprising the prodrug described herein would generate a $T_{amx}$ value of released quetiapine its active metabolite and/or derivative and their combination—that is longer thin the $T_{max}$ value produced by unconjugated quetiapine when administered at equimolar doses. In another embodiment the compositions comprising the prodrug described herein would generate a $T_{max}$ value of released quetiapine that is similar to the $T_{max}$ value produced by unconjugated quetiapine, when administered at equimolar doses.

In another embodiment, the compositions comprising the prodrug described herein would have reduced interindividual variability either due to increased bioavailability in one aspect, or due to a modified metabolic pathway in another aspect, or due to a combination of both in yet another aspect.

In another embodiment, the compositions comprising the prodrug described herein would alter the metabolic pathway of the released quetiapine when compared to unmodified quetiapine. This new metabolism may decrease interindividual variability and/or reduce side-effects associated with unconjugated quetiapine or any of its metabolites, pharmaceutically acceptable salts thereof, derivatives thereof or their combination.

In yet another embodiment, the compositions comprising the prodrug described herein would decrease the number and/or amount of metabolites—active, inactive, toxic or non-toxic—produced by unmodified quetiapine. This may decrease interindividual variability and/or reduce side-effects associated with the administration of unconjugated quetiapine.

In a further embodiment, the compositions comprising the prodrug described herein would increase the amount of active metabolites when compared to unmodified quetiapine. This may improve the therapeutic efficacy of the parent drug.

Although quetiapine is not a controlled substance, there have been increasing reports of its misuse via oral, intranasal, and intravenous routes to exploit its potent sedative and anxiolytic properties. Some of its street names include "quell", "baby heroin" and "Susie-Q". In some embodiments, the compositions comprising the prodrug described herein may not be hydrolyzed efficiently when administered by non-oral routes. As a result, these prodrugs may generate plasma concentrations of released quetiapine that are lower when compared to free quetiapine when administered intravenously ("injected") or intranasally ("snorted").

In one embodiment, provided herein is a quetiapine or its active metabolite, conjugated to the standard amino acid valine as represented by any one of the structures of formulas I-IV:

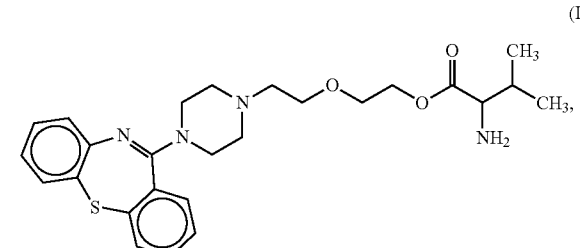

(I)

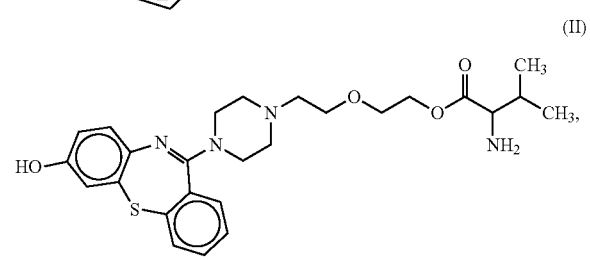

(II)

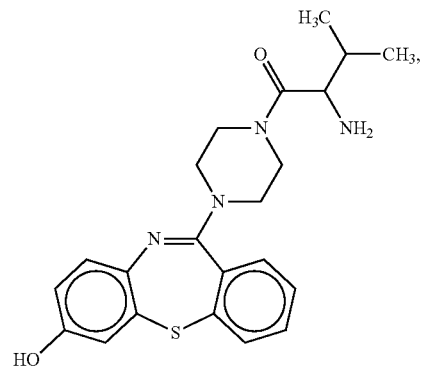

(III)

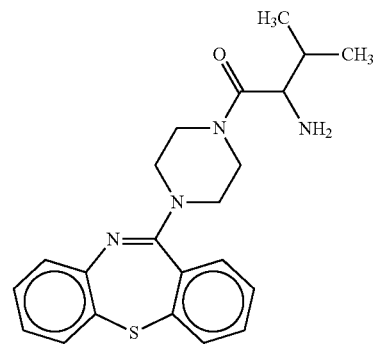

(IV)

a pharmaceutically acceptable salt thereof, a derivative thereof or their combination.

In another embodiment, provided herein is a quetiapine or its active metabolite, conjugated to the standard amino acid phenylalanine, as represented by any one of the structures of formulas V-VIII:

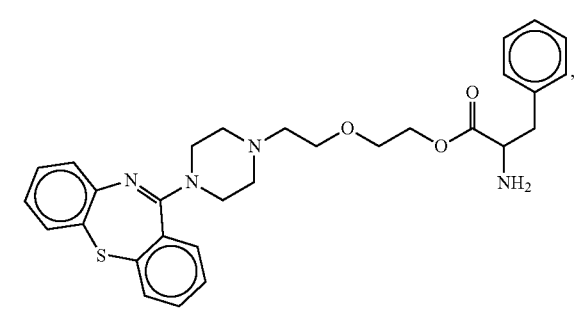

(V)

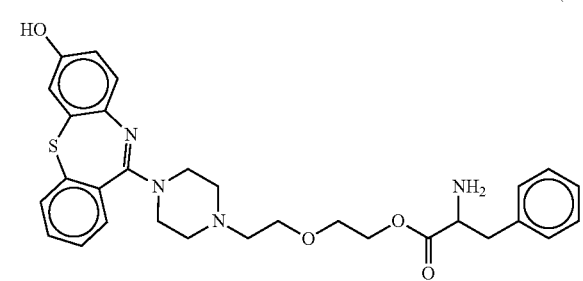

(VI)

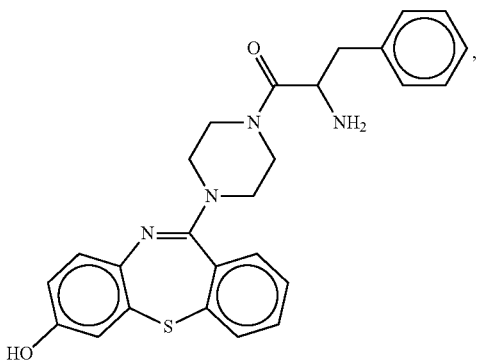

(VII)

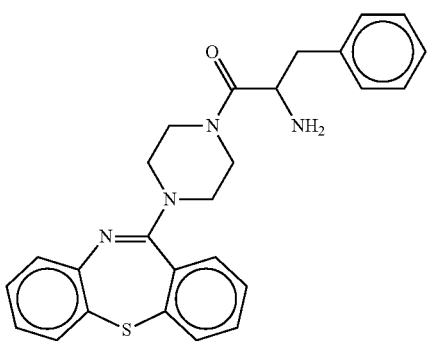

(VIII)

a pharmaceutically acceptable salt thereof, a derivative thereof or their combination.

In one embodiment, the salt of the conjugate of quetiapine or an active metabolite and/or derivative thereof and a standard, non-standard and or synthetic amino acid, such as any one of the structures represented by formulas I-VI hereinabove, is a hydrochloride salt, a hydrobromide salt, a hydroiodide salt, a sulfate, a phosphate, an organic acid salt, a nitrate, or a mixture thereof. In another embodiment, the organic acid is a mesylate salt, a besylate salt, a tosylate salt, a benzoate, an oxalate, a fumarate, a triflate, a citrate, a malate, or a tartarate.

Formulation Examples

The prodrugs provided in the compositions and methods herein are primarily geared towards oral dosage forms. These dosage forms include but are not limited to tablet, capsule, caplet, troche, lozenge, powder, suspension, syrup, solution or oral thin film (OTF). Embodiments of oral administration forms are capsule, tablet, solutions and OTF. The film dosage forms provide an inexpensive, convenient and immediate method for delivery of the compositions described herein without the undesirable aspects associated with certain oral or nasal delivery methods, while providing versatility, safety and patient comfort. Any effective edible "thin film" or "strip" may be used in accordance with the present invention. Unless otherwise specified or required by the context, the edible films of the present invention may be manufactured in any effective manner.

In certain embodiments, the film layer can be produced using a highly water-soluble polymer comprising a natural or synthetic water-soluble polymer. The polymer preferably has good film moldability, produces a soft flexible film, and is safe for human consumption. In another embodiment, one such polymer can be a water-soluble cellulose derivative like hydroxypropyl cellulose (HPC), methyl cellulose, hydroxypropyl alkylcellulose, carboxymethyl cellulose or the salt of carboxymethyl cellulose or the polymer can comprise an acrylic acid copolymer or its sodium, potassium or ammonium salt. The acrylic acid copolymer or its salt can be combined with methacrylic acid, styrene or vinyl type of ether as a comonomer, poly vinyl alcohol, poly vinyl pyrrolidone, polyalkylene blycol, hydroxy propyl starch, alginic acid or its salt, poly-saccharide or its derivatives such as trangacanth, bum gelatin, collagen, denatured gelatin, and collagen treated with succinic acid or anhydrous phthalic acid. In another embodiment the powder matrix may comprise as an adhesives: poorly water-soluble cellulose derivatives including ethyl cellulose, cellulose acetate and butyl cellulose; shellac; higher fatty acids including steric acid and palmitic acid. The following can also, without limitation, be used to produce the film layer: pullulan, maltodextrin, pectin, alginates, carrageenan, guar gum, other gelatins, etc. The thickness of the film layer can vary as desired, but typically is in the range of 0.01 mm to 3.00 mm, preferably 0.03 mm to 1.00 mm. In one embodiment, the standard, non-standard, or synthetic amino acid used in the conjugates provided herein will be affected by the composition of the OTF.

Solid dosage forms can include the following types of excipients: antiadherents, binders, coatings, disintegrants, fillers, flavors, colors, glidants, lubricants, preservatives, sorbents and sweeteners.

For oral administration, the conjugates can be formulated readily by combining the active compounds with pharmaceutically acceptable carriers well known in the art. Such carriers enable the conjugates provided herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in certain embodiments, fillers such as sugars, including lactose, sucrose, manioc, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as poly(vinylpyrrolidone) (PVP). If desired, in certain embodiments disintegrating agents may be added, such as cross-linked polyvinyl pyrrolidone, agar, or alginic acid or a salt thereof such as sodium alginate.

Dragee cores may be provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner. Alternatively, the active ingredient may be in powder form for constitution with a suitable vehicle, e.g., sterile, pyrogen-free water, before use. The conjugates provided herein may also be formulated in rectal compositions such as suppositories or retention enemas, using, e.g., conventional suppository bases such as cocoa butter or other glycerides.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Quetiapine was originally launched as an immediate release product (Seroquel®) with the following dosage strengths per tablet: 25 mg, 50 mg, 100 mg, 200 mg and 300 mg. Recommended daily doses typically range from 150-800 mg depending on indication and individual patient titration. In another embodiment, quetiapine is available in an extended release formulation (Seroquel XR®) with dosage strengths of 50 mg, 150 mg, 200 mg, 300 mg and 400 mg per tablet. Typical daily doses range from 300-800 mg.

In one embodiment, the conjugate of quetiapine, its antipsychotic-active metabolite and/or active derivatives; and a standard, non-standard, or synthetic amino acid used in the compositions provided herein, a salt thereof, a derivative thereof or their combination is present in an amount of between about 1 mg and 2000 mg per dose form. In another embodiment, conjugates of quetiapine or its antipsychotic-active metabolite and/or active derivatives thereof, their salt or pharmaceutically acceptable salt are present in the compositions provided herein in an amount that is therapeutically effective. In one embodiment, conjugates of quetiapine or its antipsychotic-active metabolite and/or active derivatives thereof, their salt or pharmaceutically acceptable salt are present in the compositions provided herein in an amount of between about 150 and 800 mg per dose form. In one embodiment, conjugates of quetiapine or its antipsychotic-active metabolite and/or active derivatives thereof, their salt or pharmaceutically acceptable salt are present in the compositions provided herein in an amount of between about 1 and 100 mg per dose form, or between about 100 and 200 mg/dose, or between about 200 and 300 mg/dose, or between about 300 and 400 mg/dose, or between about 400 and 500 mg/dose, or between about 500 and 600 mg/dose, or between about 600 and 700 mg/dose, or between about 700 and 800 mg/dose, or between about 800 and 900 mg/dose, or between about 900 and 1000 mg/dose, or between about 350 and 400 mg/dose, or between about 20 and 30 mg/dose, or between about 50 and 150 mg/dose, or between about 1 and 375 mg/dose, each a discrete embodiment of the amount conjugates of quetiapine or its antipsychotic-active metabolite and/or active derivatives thereof, their salt or pharmaceutically acceptable salt are present in the compositions provided herein. In one embodiment, conjugates of quetiapine or its antipsychotic-active metabolite and/or active derivatives thereof, their salt or pharmaceutically acceptable salt are present in the compositions provided herein in an amount of between about 1000 and 2000 mg per dose form. In another embodiment, conjugates of quetiapine or its antipsychotic-active metabolite and/or active derivatives thereof, their salt or pharmaceutically acceptable salt are present in the compositions provided herein in an amount of between about 1000 and 1250 mg per dose form, or between about 1250 and 1500 mg per dose form, or between about 1500 and 1750 mg per dose form, or between about 1750 and 2000 mg per dose form, or between about 1000 and 1500 mg per dose form, or between about 1500 and 2500 mg per dose form, in other discrete embodiments.

Doses of the amino acid-quetiapine conjugate prodrugs described herein can be higher or lower than doses of unconjugated quetiapine depending on their molecular weight, the respective weight-percentage of quetiapine as part of the whole conjugate or conjugate salt and their bioavailability (with respect to released quetiapine). Dose conversion from quetiapine fumarate to quetiapine prodrug are performed in one embodiment, using the following formula:

$$\text{Dose(QTP prodrug)}=f_{BA}\times[\text{dose(QTP hemifumarate)}\times(\text{molecular weight(QTP prodrug)}/441.95 \text{ g/mol})]$$

Wherein:
QTP=quetiapine
$f_{BA}$=correction factor accounting for differences in bioavailability between unmodified quetiapine and the compositions comprising the prodrug described herein. This correction factor is specific for each prodrug with $f_{BA} \leq 1$ in certain embodiments. In one embodiment, the conjugate of quetiapine, an active metabolite or derivative thereof and a standard, non-standard and/or synthetic amino acid, a salt thereof, a derivative thereof or their combination is present in an amount calculated according to the formula provided herein, referred to as "equivalent dose" to certain unconjugated quetiapine doses.

Quetiapine is a dibenzothiazepine derivative. In pharmacokinetic studies quetiapine is rapidly absorbed after oral administration, with median time to reach maximum observed plasma concentration ranging from 1 to 2 hours. Absolute bioavailability is estimated at 9%, with a relative bioavailability from orally administered tablets compared with a solution of almost 100%. Administration with foods other than fatty foods, has minimal effects on the absorption of the API. The drug is approximately 83% bound to serum proteins. Linear pharmacokinetics are observed in the clinical dose range (up to 375 mg twice daily). The terminal half-life time for the drug's elimination is about 7 hours, with the primary route of elimination being through hepatic metabolism.

In one embodiment, the term "relative bioavailability" refers to $AUC_{(0-\infty)}$ for a specific orally administered composition expressed as a percentage of $AUC_{(0-\infty)}$ for an orally administered formulation of the active ingredient at the same dosage rate. The term "$C_{max}$" refers to the maximum observed blood plasma concentration or the maximum blood plasma concentration calculated or estimated from a concentration/time curve, and is expressed in units of ng/ml. The term "$T_{max}$" refers to the time after administration at which $C_{max}$ occurs, and is expressed in units of hours (h).

In one embodiment, the relative bioavailability of the compositions described herein is increased by between about 9 and 100% when administered orally compared with oral administration of unconjugated quetiapine, an active metabolite and/or an active derivative thereof. In another embodiment, the relative bioavailability is increased by between about 25 and 100%, or between about 50 and 100%, or between about 75 and 100%, or between about 100 and 125%, or between about 125 and 150%, or between about 150 and 175%, or between about 175 and 200%, or between about 9 and 25%, when administered orally compared with oral administration of unconjugated quetiapine, an active metabolite and/or an active derivative thereof in other discrete embodiments.

Quetiapine is metabolised in one embodiment by cytochrome P450 (CYP) 3A4 and/or 2D6 in certain other embodiments. Eleven metabolites were identified as formed through hepatic oxidation, with three of those found to be pharmacologically active. In one embodiment, the metabolites are conjugated to the amino acids described herein and are administered either alone or in combination with the quetiapine conjugates compositions described herein and used in the methods described. Accordingly, in one embodiment, provided herein is a composition for treating a psychiatric disorder in a subject, comprising a conjugate of 7-hydroxy-quetiapine (7-OH-QTP) represented by the structure of Formula IX:

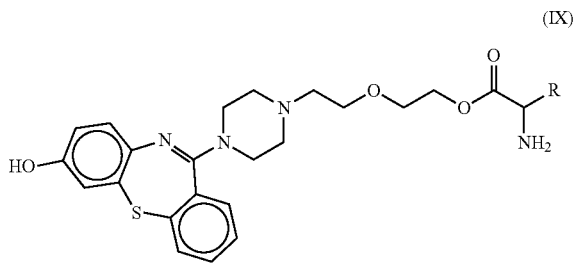

(IX)

and an amino acid, a salt thereof, a derivative thereof or their combination. In another embodiment, provided herein is a composition for treating a psychiatric disorder in a subject, comprising a conjugate of 7-hydroxy-N-desalkyl-quetiapine (7-OH-norQTP) represented by the structure of Formula X:

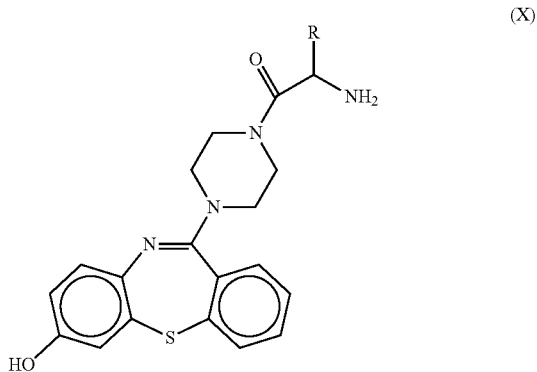

(X)

and an amino acid, a salt thereof, a derivative thereof or their combination. In another embodiment, provided herein is a composition for treating a psychiatric disorder in a subject, comprising a conjugate of N-desalkyl-quetiapine (norQTP) represented by the structure of Formula XI:

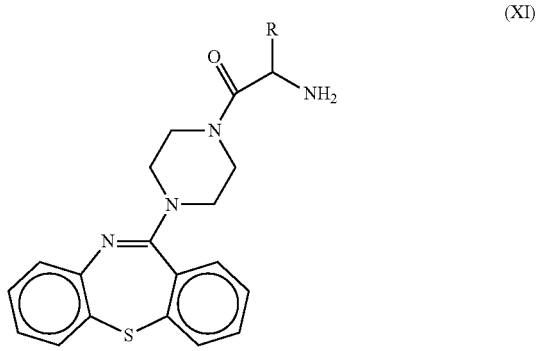

(XI)

and an amino acid, a salt thereof, a derivative thereof or their combination.

In one embodiment, oral clearance of unconjugated quetiapine declines with age. In another embodiment, relative bioavailability of amino acid-quetiapine conjugates is higher at every age, thereby leading to reduced dosage for every indication and minimizing side-effects. Since quetiapine is primarily metabolized by CYP3A4, dosage adjustment may be necessary in another embodiment when coadministered with phenytoin, thioridazine retinoic acid, rifampicin, ketoconazole, carbamazepine or other potent CYP3A4 agonists, antagonists or modulators. In one embodiment, the choice of amino-acid conjugated to quetiapine will affect the dosage adjustment necessary.

Advantages

Conjugation of quetiapine or its active metabolite and/or active derivative thereof to amino acids as described herein, has a number of advantages that may include: Reduced inter-individual variability in plasma concentrations vs. free quetiapine Increased bioavailability
Improved side-effect profile
Less potential for toxic metabolites
Less inactive metabolites
Improved solubility
Reduced potential for drug abuse In one embodiment, the compositions comprising quetiapine conjugated to an amino acid, further comprise a carrier, excipient, lubricant, flow aid, processing aid or diluent, wherein said carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetener, a film forming agent, or any combination thereof.

In one embodiment, the composition is a controlled release composition. In another embodiment, the composition is an immediate release composition. In one embodiment, the composition is a liquid dosage form. In another embodiment, the composition is a solid dosage form.

In one embodiment, the term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the amino acid-quetiapine conjugates described herein and/or their metabolites and derivatives, are prepared in another embodiment, from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, in another embodiment, the appropriate acid or base with the compound.

In one embodiment, the term "pharmaceutically acceptable carriers" includes, but is not limited to, 0.01-0.1 M and preferably 0.05 M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In one embodiment the level of phosphate buffer used as a pharmaceutically acceptable carrier is between about 0.01 to about 0.1 M, or between about 0.01 to about 0.09 M in another embodiment, or between about 0.01 to about 0.08 M in another embodiment, or between about 0.01 to about 0.07 M in another embodiment, or between about 0.01 to about 0.06 M in another embodiment, or between about 0.01 to about 0.05 M in another embodiment, or between about 0.01 to about 0.04 M in another embodiment, or between about 0.01 to about 0.03 M in another embodiment, or between about 0.01 to about 0.02 M in another embodiment, or between about 0.01 to about 0.015 in another embodiment.

The pharmaceutical preparations comprising the compositions used in one embodiment in the methods provided herein can be prepared by known dissolving, mixing, granulating, or tablet-forming processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water for injection and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions. In one embodiment, using aliphatic or aromatic amino acids, increases solubility or dispersibility of quetiapine conjugates when compared to unconjugated quetiapine, its active metabolite and/or derivative in the oily vehicles described herein.

In addition, the composition described in the embodiments provided herein, can contain minor amounts of auxiliary substances such as wetting or emulsifying agents, pH buffering agents which enhance the effectiveness of the active ingredient.

The amino acid-quetiapine conjugate described herein is administered in another embodiment, in a therapeutically effective amount. The actual amount administered, and the rate and time course of administration, will depend in one embodiment, on the nature and severity of the condition being treated. Prescription of treatment, e.g., decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

The compositions of the present invention are formulated in one embodiment for oral delivery, wherein the active compounds may be incorporated with excipients and used in the form of ingestible tablets, buccal tablets, troches, capsules, elixirs, suspensions, syrups, wafers, and the like. The tablets, troches, pills, capsules and the like may also contain the following: a sweetening agent, such as sucrose, lactose or saccharin that may be added or a flavoring agent, such as peppermint, oil of wintergreen, or cherry flavoring. When the dosage unit form is a capsule, it may contain, in addition to materials of the types described hereinabove, a liquid carrier. Various other materials may be present as coatings or to otherwise modify the physical form of the dosage unit. For instance, tablets, pills, or capsules may be coated with shellac, sugar, or both. Syrup of elixir may contain the active compound, sucrose as a sweetening agent, methyl and propylparabens as preservatives, a dye and flavoring, such as cherry or orange flavor. In addition, the API may be incorporated into sustained-release, pulsed release, controlled release or postponed release preparations and formulations.

In another embodiment, the term "dosage unit" or "dose" refers to the portion of a pharmaceutical composition that contains a single unit dose of the active ingredient. For purposes of the disclosure presented herein, a dose unit can be in the form of a discrete article such as a tablet, capsule or a suppository, or can be a measurable volume of a solution, suspension or the like containing a unit dose of the active ingredient. The term "unit dose" refers in one embodiment to an amount of active ingredient intended for a single oral administration to a subject for treatment of a psychiatric condition or disorder. Treatment of a psychiatric condition or disorder, comprising mediating or binding of a dopamine and/or serotonin and/or histamine receptor, may require periodic administration of unit doses of the compositions described herein, for example one unit dose two or more times a day, one unit dose with each meal, one unit dose every four hours or other interval, or only one unit dose per day.

Controlled or sustained release compositions include formulations in lipophilic depots (e.g., fatty acids, waxes, oils). Also comprehended by the invention are particulate compositions coated with polymers (e.g., poloxamers or poloxamines).

In another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 [1984]). Other controlled release systems are discussed in the review by Langer (Science 249: 1527-1533 [1990]).

In one embodiment, the carriers for use within such compositions are biocompatible, and/or biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture, lower pH or temperature threshold in other discrete embodiments. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In one embodiment, the term "administering" refers to bringing a subject in contact with the compositions provided herein. For example, in one embodiment, the compositions provided herein are suitable for oral administration, whereby bringing the subject in contact with the composition comprises ingesting the compositions. A person skilled in the art would readily recognize that the methods of bringing the subject in contact with the compositions provided herein, will depend on many variables such as, without any intention to limit the modes of administration; age, pre-existing conditions, other agents administered to the subject, the severity of symptoms, subject weight or propensity to gain weight, refraction to other medication and the like. In one embodiment, provided herein are embodiments of methods for administering the compounds of the present invention to a subject, through any appropriate route, as will be appreciated by one skilled in the art.

Methods of Synthesis

A general synthetic scheme for the synthesis of a prodrug of this invention typically consists of the following steps:
1. Protection of the amino acid, if applicable.
2. Activation of the carboxylic group, if not already in activated form.
3. Addition of activated amino acid to quetiapine or vice versa in the presence of base
4. Removal of amino acid protecting groups, if applicable.

Figure 7:
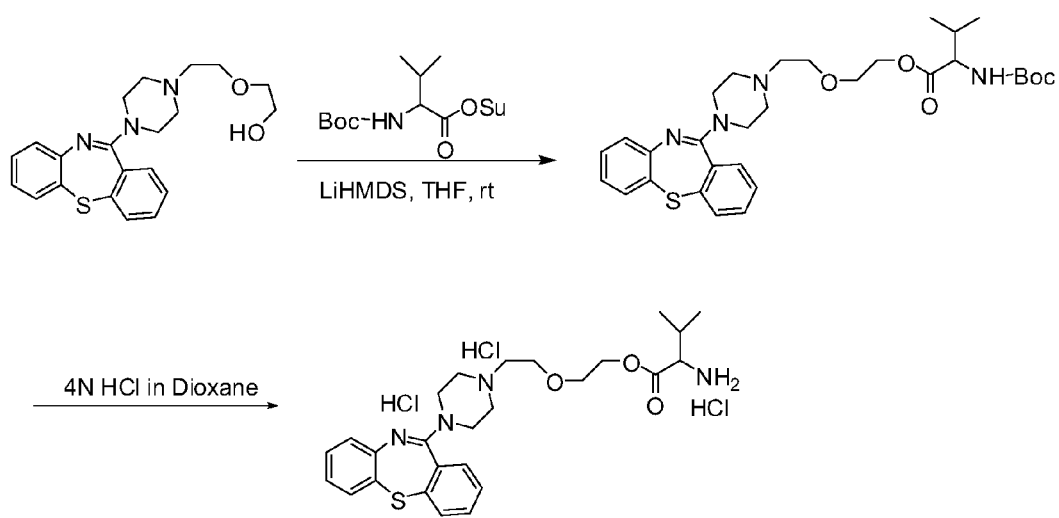
FIG. 7 shows a schematic of the process of synthesis of the valine-quetiapine conjugate.

Accordingly and in one embodiment, provided herein is a method of conjugating quetiapine or an active metabolite and/or derivative thereof and an amino acid comprising the steps of: in the presence of a base, attaching an amine-protected amino acid to quetiapine or its active metabolite; followed by deprotecting the amine-protected amino acid moiety, thereby, creating a carboxylic ester between quetiapine or an active metabolite and/or derivative thereof and a standard, non-standard or synthetic amino acid. An schematic of an exemplary process of synthesis of a valine-quetiapine conjugate is provided in FIG. 7.

The carboxylic acid group of the amino acid is activated in one embodiment in order to react with quetiapine to produce appreciable amounts of conjugate. The amino acids can be activated in another embodiment, by synthesizing esters of N-hydroxy succinimide (NHS). Other activating agents include but are not limited to the following: N,N'-dicyclohexylcarbodiimide (DCC), N-(3-dimethylaminopropyl)-N'-ethylcarbodiimide (EDCI), N,N'-diisopropyl-carbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl) D-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl)uronium tetrafluoroborate (TSTU) or other ammonium-based reagents.

Accordingly and in one embodiment, provided herein is a method of conjugating quetiapine or its active metabolite and/or active derivative thereof and an amino acid comprising the steps of: in the presence of a base, attaching an amine-protected amino acid to quetiapine or its active metabolite; followed by deprotecting the amine-protected amino acid moiety, thereby conjugating quetiapine or an active metabolite and/or derivative thereof and an amino acid. In one embodiment, the amine-protected amino acid further comprises a protected side chain residue on the amino acid.

It may be necessary to attach one or more protecting groups to any additional reactive functional groups that may interfere with the coupling to quetiapine. Any suitable protecting group may be used depending on the type of functional group and reaction conditions. The protective group may be any of those commonly used in a process known by those skilled in the art. In one embodiment a protective group is for an amino, thiol, hydroxy, phenol or carboxyl group used in common preparations of amino acids. Some protecting group examples include but are not limited to: acetyl (Ac), tert-butyloxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, etc). In another embodiment, the amino acid residue protecting group is acetyl, propionyl, butyryl, phenylacetyl, benzoyl, toluyl, POA, methoxycarbonyl, ethoxycarboryl, 2,2,2-trichloroethoxycarbonyl, 2-iodoethoxycarbonyl, 4-methoxybenzyloxycarbonyl, 4-methoxy-2,3,6-trimethylbenzenesulfonyl (Mtr), 2,2,4,6,7-pentamethyldihydrobenzofuran-5-sulfonyl (Pbf) or 2,2,5,7,8-pentamethyl-chroman-6-sulfonyl (Pmc).

In another embodiment, the protective group is not particularly limited as long as it is a protective group known to protect the amino group or the side chain group. Examples of useful protective groups are those described in T. W. Greene, "Protective groups in Organic Synthesis", A Wiley-Interscience Publication, John-Wiley & Sons, New York, 1981, pp. 218-287. Specific examples include but are not limited to substituted oxycarbonyl groups, such as lower alkyloxycarbonyl groups in another embodiment, i.e., $C_{2-7}$ straight-chain or branched-chain lower alkyloxycarbonyl groups. The protective group for carboxyl on the group side chain is not specifically limited as long as it is a conventional protective group known to form an ester or an ether with a carboxyl group. Examples are $C_{1-6}$ straight-chain or branched-chain substituted or unsubstituted lower alkyl groups such as methyl, ethyl, propyl, butyl, tert-butyl, hexyl and trichloroethyl; substituted or unsubstituted aralkyl groups such as benzyl, p-nitrobenzyl, p-methoxybenzyl and diphenylmethyl; acyloxyalkyl groups such as acetoxymethyl, acetoxyethyl, propionyloxyethyl, pivaloyloxypropyl, benzoyloxymethyl, benzoyloxyethyl, benzylcarbonyloxymethyl and cyclohexylcarbonyloxymethyl; alkoxyalkyl groups such as methoxymethyl, ethoxymethyl and benzyloxymethyl; and other groups such as tetrahydropyranyl, dimethylaminoethyl, dimethylchlorosilyl and trichlorosilyl. Preferred are substituted or unsubstituted alkyl groups and substituted or unsubstituted aralkyl groups.

A base may be required at any step of the synthesis of amino acid conjugates of quetiapine. Suitable bases include but are not limited to 4-methylmorpholine (NMM), 4-(dimethylamino)pyridine (DMAP), N,N-diisopropylethylamine, lithium bis(trimethylsilyl)amide, lithium diisopropylamide (LDA); any alkali metal tert-butoxide (e.g., potassium tert-butoxide), any alkali metal hydride (e.g., sodium hydride), any alkali metal alkoxide (e.g., sodium methoxide), triethylamine or any other tertiary amine.

An acid may be required to remove certain protecting groups. Suitable acids include but are not limited to hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid.

Appropriate solvents that can be used for any reaction in the synthetic scheme of any amino acid conjugate of quetiapine include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert-butyl ether (MTBE), isopropanol, isopropyl acetate, diisopropyl ether, tetrahydrofuran, toluene, xylene or water.

In one embodiment, the step of deprotecting the amine-protected amino acid moiety is preceded by a step of deprotecting the side chain on the amino acid. In another embodiment, the step of deprotecting the amine-protected amino acid, is done simultaneously with deprotecting the side chain on the amino acid. In another embodiment, the step of deprotecting the side chain is preceded by a step of deprotecting the amine-protected amino acid moiety.

In one embodiment, the compounds conjugated using the methods provided herein, are used in the compositions and methods described herein. Accordingly, and in another embodiment, provided herein is quetiapine, its active metabolite and/or derivative; conjugated to a standard, non-standard and/or synthetic amino acid synthesized by attaching an amine-protected amino acid in the presence of a base to quetiapine or its active metabolite and/or derivative; followed by deprotecting the amine-protected amino acid moiety, thereby conjugating quetiapine, an active metabolite and/or an active derivative thereof and an amino acid.

In another embodiment, the protecting groups prevent undesired or deleterious reactions from taking place at the alpha-amino group during the formation of a new carboxyl ester bond between the unprotected carboxyl group of the standard, non-standard and/or synthetic amino acid; and the free non-binding electrons on the quetiapine, its active metabolite and/or derivative. A series of chemical steps subsequently protect the amino acid and prepare it for coupling to the quetiapine, its active metabolite and/or derivative without undesirable side reactions. In one embodiment, "protecting" an acid prevents undesired side or competing reactions, and "deprotecting" an acid makes its functional group(s) available for a desired reaction and/or obtaining the final conformation of the prodrug.

Deprotection is carried out in one embodiment with a mild base treatment (e.g., picrodine or piperidine, for a non-limiting example) for temporary protective groups, while in another embodiment; permanent side-chain protecting groups are removed by moderate acidolysis (e.g., trifluoroacetic acid (TFA) as a non-limiting example).

In one embodiment, the compositions described herein are used to carry out the methods provided herein.

In one embodiment, the psychiatric disorder sought to be treated using the compositions provided herein is bipolar disorder (BPD) and the inpatient receives conjugated quetiapine at an equimolar dose in the amount of 375 mg daily of unconjugated quetiapine, corresponding to a dose of over 375 mg daily due to the higher bioavailability, or altered metabolism of the conjugated quetiapine as described herein, resulting in a larger difference and shorter duration in depressive symptoms on admission and at discharge using the Beck-Rafaelsen Mania Scale (MAS) and/or the Montgomery Asberg depression rating scale (MADRS), respectively.

In another embodiment, the psychiatric disorder sought to be treated using the compositions provided herein is schizophrenia, and the inpatient receives conjugated quetiapine at an equimolar dose in the amount of 450 mg daily of unconjugated quetiapine, corresponding to a dose of over 450 mg daily due to the higher bioavailability or altered metabolism of the conjugated quetiapine as described herein, resulting in a larger difference and shorter duration in psychotic symptoms on admission and at discharge using Brief Psychiatric Rating Scale (BPRS), Clinical Global Impression (CGI), Positive And Negative Syndrome Scale (PANSS) and the like. Using the compositions described herein, results in another embodiment in increased interval between psychotic episodes, decrease in severity of the episode and a lesser loss in cognitive abilities following an episode.

In one embodiment, provided herein is a method of treating a psychiatric disorder requiring the binding of dopamine receptor, serotonin receptor, or both in a subject, comprising the step of administering to the subject a composition comprising therapeutically effective amount of quetiapine, an active metabolite and/or an active derivative thereof, conjugated to an amino acid, a pharmaceutically acceptable salt or derivative thereof, thereby binding to a dopamine receptor, a serotonin receptor, or both.

In another embodiment, provided herein is a method of treating schizophrenia or bipolar disorder in a subject in need thereof, comprising the step of administering to the subject a composition comprising therapeutically effective amount of quetiapine, an active metabolite and/or an active derivative thereof, conjugated to an amino acid, a pharmaceutically acceptable salt or derivative thereof, thereby binding to a dopamine receptor, a serotonin receptor, or both.

In another embodiment, due to the higher relative bioavailability the unit dose used for treating the disorders described herein, will be adjusted downward, leading to a decrease in number and severity of side-effects.

In one embodiment, the disorder requiring the binding of dopamine receptor(s), serotonin receptor(s), or both in a subject is obsessive-compulsive disorder (OCD), post-traumatic stress disorder (PTSD), restless legs syndrome, autism, alcoholism, depression, insomnia, hyperprolactinemia or Tourette syndrome.

By way of example, Restless Leg Syndrome (RLS) has been treated with non-ergot dopamine agonists, with quetiapine showing remarkable efficacy. In one embodiment, provided herein is a method of treating RLS in a subject in need thereof, comprising the step of orally administering to the subject a therapeutically effective amount of a composition comprising quetiapine, an active metabolite and/or active derivative thereof conjugated to a standard, non-standard and/or synthetic amino acid, a pharmaceutically acceptable salt thereof or their combination.

Likewise and in another embodiment, post-traumatic stress disorder (PTSD) refers in one embodiment to a chronic mental illness, causing occupational disability, psychiatric and medical morbidity and severe psychosocial distress. The prevalence of PTSD in the general population in the U.S. in 2006 was estimated to be 7.8%. Core symptoms of PTSD include recurrent re-experiencing of the trauma in the form of intrusive memories, nightmares and flashbacks; avoidant behaviors; and autonomic arousal. In addition to the core PTSD symptoms, patients with PTSD also exhibit irritability, impulsivity, depression and aggression. PTSD is often difficult to treat, with recent initiatives focusing on the role of serotonin in the neuroregulation of PTSD. The neurotransmitter serotonin influences mood, aggression, arousal, anxiety, sleep, learning, nociception, fear and appetite. Likewise, dopamine neurotransmission dysfunction has been shown to be responsible for symptoms such as paranoia, hallucinations, increased startle response and their combination. Physiologically, the density of platelet serotonin-uptake sites, as determined by paroxetine binding, was significantly decreased in patients with PTSD, compared with normal controls. Clinical studies showed the benefits of treatment of PTSD symptoms with a 5-HT$_{1A}$ partial agonist, of which quetiapine metabolite N-desalkyl-quetiapine is one.

In one embodiment, the term "treating" refers to abrogating, substantially inhibiting, slowing or reversing the progression of a disease, substantially ameliorating clinical symptoms of a disease or substantially preventing or delaying the appearance of clinical symptoms of a disease.

In one embodiment, the compositions provided herein, which in another embodiment are used in the methods described herein; are administered to a subject in need thereof as part of a combination therapy with other medication that is specific for the indication sought to be treated. A person skilled in the art would readily recognize that combination therapy as described in the methods and compositions provided herein, could be administered either simultaneously or consecutively and so long as they are administered for the same indication, would be encompassed by the description provided herein.

Accordingly and in one embodiment lithium or divalproex in another embodiment are used in certain embodiments as adjunct therapies with the compositions provided herein.

In one embodiment, provided herein is the use of a therapeutically effective amount of a conjugate of quetiapine, its active metabolite and/or active derivative; and a standard, non-standard and or synthetic amino acid in a medicament for the treatment of a disorder associated with serotonin, dopamine or histamine dysfunction in a subject in need thereof.

In the present specification, use of the singular includes the plural except where specifically indicated.

In one embodiment, the term "subject" refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Example 1

Oral Pharmacokinetic Data

Plasma concentrations of quetiapine released from prodrug conjugates as described herein were dosed as oral solutions in rats and compared to an equimolar solution of quetiapine dihydrochloride. Although the commercial form of quetiapine (Seroquel®) is a fumarate salt, the dihydrochloride salt was used as comparator because the fumarate is not soluble enough to be dosed efficiently via oral gavage in rats.

Figure 4:
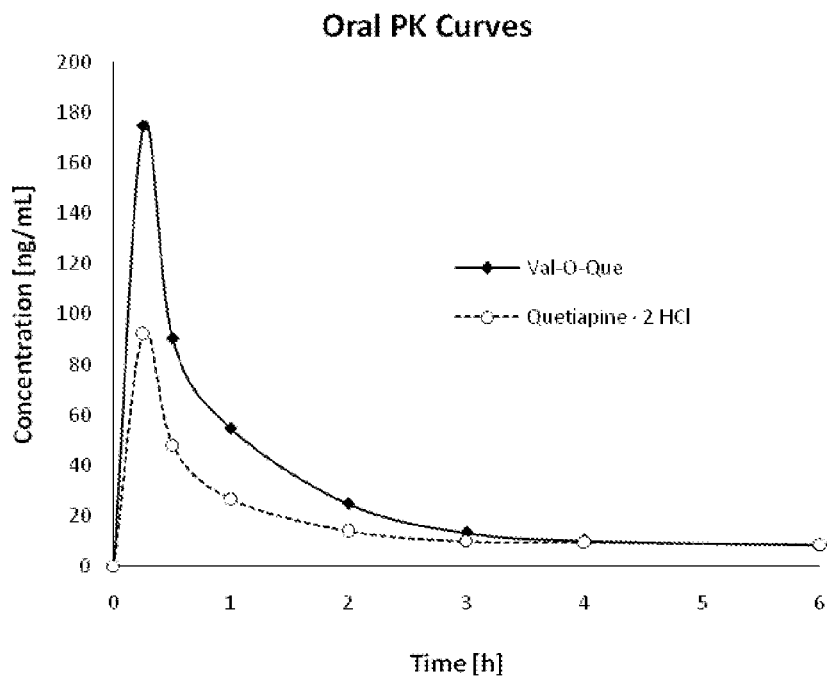
FIG. 4 shows the oral PK profile of quetiapine released from valine-quetiapine compared to an equimolar dose of quetiapine dihydrochloride in rats.
Figure 5:
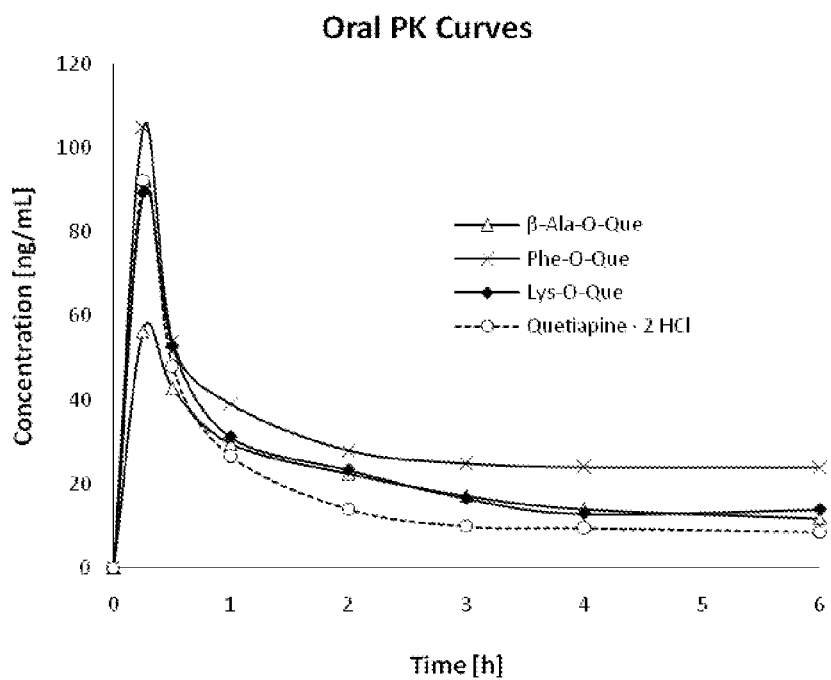
FIG. 5 shows the oral PK profiles of quetiapine released from β-alanine-quetiapine, phenylalanine-quetiapine and lysine-quetiapine compared to an equimolar dose of quetiapine dihydrochloride in rats.
Figure 6:
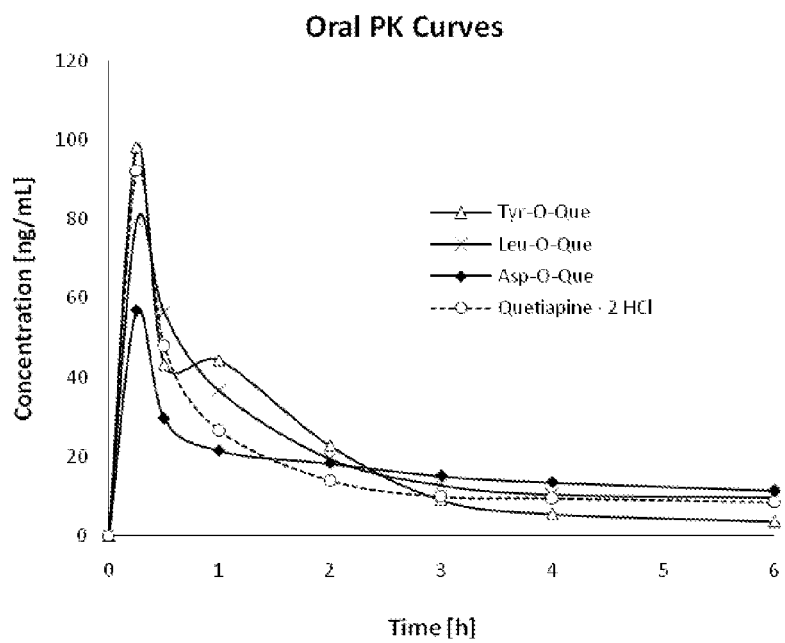
FIG. 6 shows the oral PK profiles of quetiapine released from tyrosine-quetiapine, leucine-quetiapine and aspartate-quetiapine compared to an equimolar dose of quetiapine dihydrochloride in rats.

Generally and as shown in FIGS. 4-6, plasma concentrations of released quetiapine varied depending on the attached amino acid. For the provided examples, the systemic exposure of released quetiapine ranged from 99-175% (%-AUC compared to quetiapine dihydrochloride). Valine-quetiapine showed the highest relative %-AUC value of 175%. $C_{max}$ values varied between 61-189% (%-$C_{max}$ compared to quetiapine dihydrochloride) with valine-quetiapine producing the highest relative %-$C_{max}$ value of 189%. $T_{max}$ values were similar for all examples.

Example 2

General Synthesis of Amino Acid-Quetiapine Conjugates

A general synthetic scheme for the synthesis of a prodrug of this invention typically consists of the following steps:

1. Protection of the amino acid, if applicable.
2. Activation of the carboxylic group, if not already in activated form.
3. Addition of activated amino acid to quetiapine or vice versa in the presence of base
4. Removal of amino acid protecting groups, if applicable.

To a solution of quetiapine (1 mmol) in TI-IF (10 mL) was added LiN(TMS)$_2$ (1.5 mmol) at room temperature. The solution was stirred for 30 min. at room temperature. N-protected amino acid succinimidyl ester (1.05 mmol) in THF (10 mL) was added dropwise. The mixture was stirred for an additional 30 min. at room temperature, subsequently poured into an aqueous solution of ammonium chloride (200 mL) and extracted with EtOAc (2×200 mL). The organic layer was washed with aqueous NH$_4$Cl (2×100 mL) and brine (2×100 mL), dried over anhydrous Na$_2$SO$_4$ and evaporated to dryness to yield the N-protected amino acid-quetiapine conjugate.

The protected intermediate (1 mmol) was stirred in 4 N HCl/dioxane (10 mL) for 30 min. at room temperature and then concentrated to dryness to yield the respective hydrochloride salt of the amino acid conjugate of quetiapine.

Example 3

Synthesis of Valine-Quetiapine Phosphate (Val-QTP.H₃PO₄):

Boc-Val-QTP

To a solution of quetiapine free base 1 (7.66 g, 19.97 mmol) in THF (50 mL) was added dropwise LiN(TMS)$_2$ (24.9 mL, 24.9 mmol) and the reaction mixture was stirred at room temperature for 30 min. A solution of Boc-Val-OSu (6.9 g, 21.96 mmol) in THF (12 mL) was added dropwise over a period of 3-4 min. After 1 h, saturated aqueous NH$_4$Cl (150 mL) was added and stirred for 15 mins. EtOAc (300 mL) was added to the reaction mixture and stirred for an additional 30 min. The EtOAc layer was washed with citric acid solution [2% citric acid (100 mL)+brine (100 mL)] (2×), 5% aq. NaHCO$_3$ (1×200 mL) and brine (1×200 mL). The organic phase was dried over anhydrous Na$_2$SO$_4$ and evaporated to dryness to give the Boc-Val-QTP (11.09 g, 95%).

Val-QTP.3 HCl

Bdc-Val-QTP was dissolved in 1.25 M HCl in IPA (150 mL) and the reaction mixture was stirred at room temperature for 20 h. The volume of the reaction mixture was reduced to half and poured into IPAc (250 mL) while stirring. The precipitate was filtered, washed with IPAc (2×) and dried to give Val-QTP.3 HCl (11.01 g, 98%).

Alternate Method

Boc-Val-QTP (4.5 g, 7.7 mmol) was dissolved in IPA (25 mL) and to this solution was added 5-6 N HCl in IPA (25 mL). The brown reaction mixture was stirred overnight at room temperature. The reaction volume was reduced to half and poured into IPAc (150 mL) while stirring. The white precipitate was filtered, washed with IPAc and dried to give Val-QTP.3 HCl (4.2 g, 92%).

Val-QTP FB

Val-QTP.3 HCl (6.4 g, 10.99 mmol) was dissolved in water (50 mL) and to this solution was added saturated aq. NaHCO$_3$ (150 mL) followed by EtOAc (250 mL). The mixture was stirred for ~1 h at room temperature. The EtOAc layer was washed with sat. NaHCO$_3$ (2×) and brine, dried over Na$_2$SO$_4$ and evaporated to dryness to give Val-QTP FB (5.8 g) as an oil.

Val-QTP.H$_3$PO$_4$

To a solution Val-QTP FB (5.8 g, 10.52 mmol) in IPA (50 mL) was added dropwise 1 M H$_3$PO$_4$ solution (10.55 mL) in IPA. A white precipitate appeared after the addition. The reaction mixture was stirred for 30 min. at room temperature. The suspension was diluted with IPAc (60 mL) and stirred for an additional 30 min. The white precipitate was filtered, washed with IPAc and dried to give Val-QTP.H$_3$PO$_4$ (4.05 g).

Figure 8:
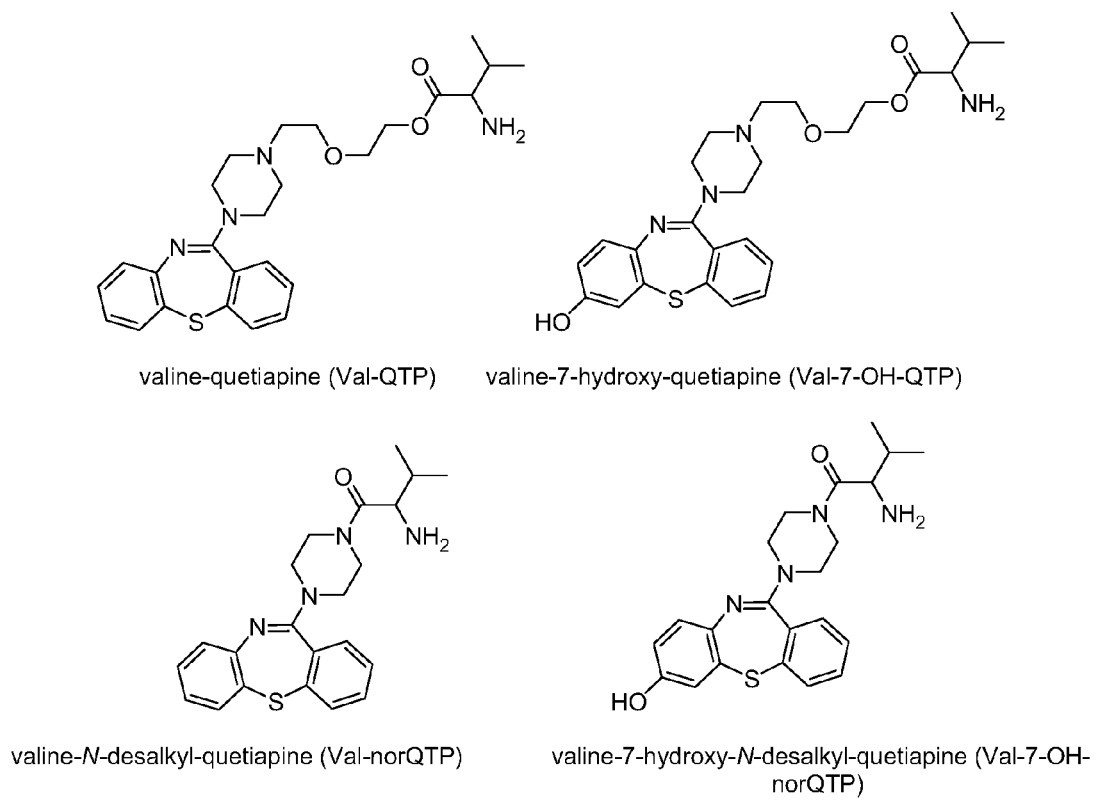
FIG. 8 shows embodiments of valine conjugates.

Several embodiments of exemplary valine conjugates of the present technology are provided in FIG. 8.

Example 4

Synthesis of phenylalanine-quetiapine trihydrochloride (Phe-QTP.3 HCl)

To a solution of quetiapine free base (0.23 g, 0.6 mmol) in THF (8 mL) was added dropwise LiN(TMS)$_2$ (0.96 mL, 0.96 mmol) and the reaction mixture was stirred for 30 min. at room temperature. A solution of Boc-Phe-OSu (0.228 g, 0.63 mmol) in THF (4 mL) was added dropwise at room temperature over a period of 5 min. After 2 h, the reaction was quenched with aqueous NH$_4$Cl (50 mL) and stirred for 15 min. The reaction mixture was extracted with EtOAc. The EtOAc layer was washed with aq. NH$_4$Cl (2×50 mL), sat. aq. NaHCO$_3$ (1×50 mL) and brine. The organic phase was dried over anhydrous Na$_2$SO$_4$ and evaporated to dryness to give Boc-Phe-QTP (0.24 g).

Boc-Phe-QTP was dissolved in 4 N HCl/dioxane (12 mL) and the reaction mixture was stirred for 4 h at room temperature. Solvents were evaporated and the residue was co-evaporated with IPAc and dried to give Phe-QTP.3 HCl (0.25 g).

Figure 9:
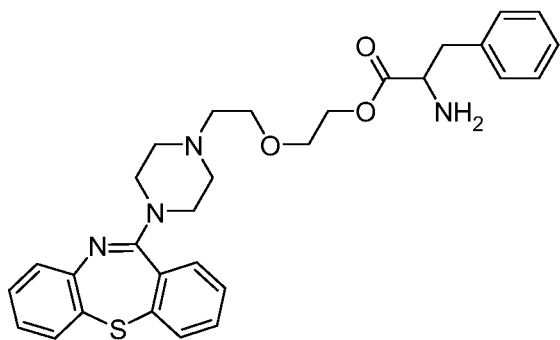
FIG. 9 shows embodiments of phenylalanine conjugates.
Figure 9:
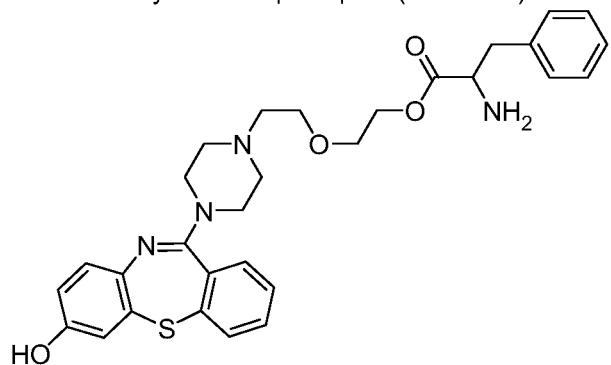
Figure 9:
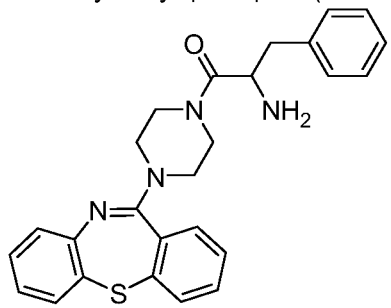
Figure 9:
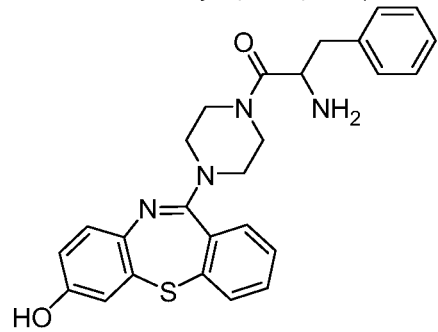

Several embodiments of exemplary phenylalanine conjugates of the present technology are provided in FIG. 9.

Example 5

Synthesis of Aspartate-Quetiapine Trihydrochloride (Asp-QTP.3 HCl)

To a solution of quetiapine free base (0.24 g, 0.62 mmol) in THF (8 mL) was added dropwise LiN(TMS)$_2$ (0.99 mL, 0.99 mmol) and the reaction mixture was stirred for 30 min. at room temperature. A solution of Boc-Asp(O$^t$Bu)-OSu (0.254 g, 0.65 mmol) in THF (4 mL) was added dropwise over a period of 5 min. After 3 h, the reaction was quenched with aqueous NH$_4$Cl (50 mL) and extracted with EtOAc (110 mL). The EtOAc layer was washed with 1% aq. NaHSO$_4$ (50 mL), sat. aq. NaHCO$_3$ (50 mL) and brine. The organic phase was dried over anhydrous Na$_2$SO$_4$ and evaporated to dryness to give Boc-Asp(O$^t$Bu)-QTP (0.265 g).

A solution of Boc-Asp(O$^t$Bu)-O-Que in 4 N HCl/dioxane (12 mL) was stirred for 8 h at room temperature. Solvents were evaporated and the residue was co-evaporated with IPAc and dried to give Asp-QTP.3 HCl (0.26 g).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A composition for treating a psychiatric disorder in a subject comprising 2-(2-(4-(dibenzo[b,f][1,4]thiazepin-11-yl)piperazin-1-yl)ethoxy)ethanol (quetiapine), conjugated to phenylalanine via an ester bond.

2. The composition of claim 1, wherein the composition has a higher relative bioavailability than non-conjugated quetiapine when administered orally.

3. The composition of claim 1, wherein the composition is formulated for oral or suppository administration.

4. The composition of claim 3, wherein the composition formulated for oral administration is a tablet, capsule, caplet, pill, troche, lozenge, liquid solution, suspension, elixir or oral thin film.

5. The composition of claim 1, wherein the conjugate is present in an amount of between about 1 mg and 2000 mg per unit dose.

6. The composition of claim 4, wherein the conjugate is present in an amount of between about 150 and 800 mg per unit dose.

7. The composition of any one of claim 5 or 6, wherein the presence of quetiapine is based on molar equivalent of unconjugated quetiapine.

8. The composition of claim 1, further comprising one or more of: lithium, divalproex, antiadherents, binders, coatings, disintegrants, fillers, flavors and colors, glidants, lubricants, preservatives, sorbents and sweeteners.

9. The composition of any one of claim 1 or 5, wherein the composition comprises a salt of the conjugate.

10. The composition of claim 9, wherein the salt is a hydrochloride salt, a hydrobromide salt, a hydroiodide salt, a sulfate, a phosphate, an organic acid salt, a nitrate, a benzoate or a mixture thereof.

11. A composition for treating a psychiatric disorder in a subject comprising quetiapine, conjugated to phenylalanine via an ester bond wherein the conjugate is represented by any one of the following structures of formulas V-VI:

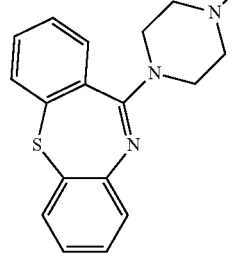
(V)

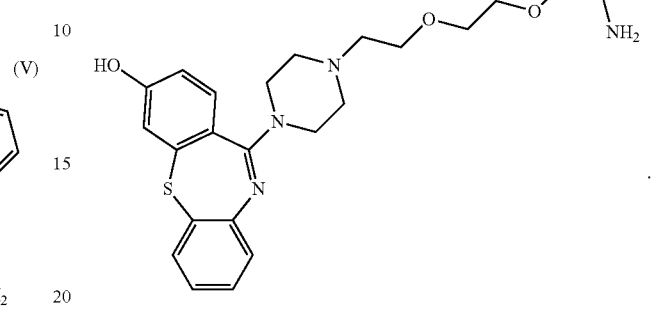
(VI)

12. A method of treating a psychiatric disorder comprising a step of administering to a subject a composition comprising a therapeutically effective amount of 2-(2-(4-(dibenzo[b,f][1,4]thiazepin-11-yl)piperazin-1-yl)ethoxy)ethanol (quetiapine), conjugated to phenylalanine via an ester bond, or a pharmaceutically acceptable salt thereof.

13. The composition of claim 10, wherein the organic acid salt is a mesylate salt, a besylate salt, a tosylate salt, an oxalate salt, a fumarate salt, a triflate salt, a citrate salt, a malate salt, or a tartarate salt.

* * * * *